United States Patent
Tada et al.

(10) Patent No.: US 9,278,071 B2
(45) Date of Patent: Mar. 8, 2016

(54) ORGANIC COMPOUND NANO-POWDER, METHOD FOR PRODUCING THE SAME AND SUSPENSION

(71) Applicant: Activus Pharma Co., Ltd., Funabashi-shi, Chiba (JP)

(72) Inventors: Takahiro Tada, Funabashi (JP); Kazuhiro Kagami, Funabashi (JP); Shiro Yokota, Funabashi (JP)

(73) Assignee: ACTIVUS PHARMA CO., LTD., Chiba (JP)

( * ) Notice: Subject to any disclaimer, the term of this patent is extended or adjusted under 35 U.S.C. 154(b) by 0 days.

(21) Appl. No.: 14/001,645

(22) PCT Filed: May 11, 2013

(86) PCT No.: PCT/JP2013/003023
§ 371 (c)(1),
(2) Date: Aug. 26, 2013

(87) PCT Pub. No.: WO2013/168437
PCT Pub. Date: Nov. 14, 2013

(65) Prior Publication Data
US 2014/0328917 A1    Nov. 6, 2014

(30) Foreign Application Priority Data
May 11, 2012  (JP) ................................. 2012-108972

(51) Int. Cl.

| | |
|---|---|
| A61K 9/50 | (2006.01) |
| A61K 9/14 | (2006.01) |
| B02C 1/00 | (2006.01) |
| A61K 9/16 | (2006.01) |
| A61K 31/12 | (2006.01) |
| A61K 31/167 | (2006.01) |
| A61K 31/192 | (2006.01) |
| A61K 31/196 | (2006.01) |
| A61K 31/405 | (2006.01) |
| A61K 31/41 | (2006.01) |
| A61K 31/445 | (2006.01) |
| A61K 31/57 | (2006.01) |
| A61K 31/573 | (2006.01) |
| A61K 31/7048 | (2006.01) |
| B02C 23/18 | (2006.01) |
| A61K 9/10 | (2006.01) |
| A61K 31/216 | (2006.01) |
| A61K 9/00 | (2006.01) |

(52) U.S. Cl.
CPC .................. *A61K 9/1682* (2013.01); *A61K 9/10* (2013.01); *A61K 9/145* (2013.01); *A61K 9/146* (2013.01); *A61K 31/12* (2013.01); *A61K 31/167* (2013.01); *A61K 31/192* (2013.01); *A61K 31/196* (2013.01); *A61K 31/216* (2013.01); *A61K 31/405* (2013.01); *A61K 31/41* (2013.01); *A61K 31/445* (2013.01); *A61K 31/57* (2013.01); *A61K 31/573* (2013.01); *A61K 31/7048* (2013.01); *B02C 23/18* (2013.01); *A61K 9/0048* (2013.01)

(58) Field of Classification Search
None
See application file for complete search history.

(56) References Cited

U.S. PATENT DOCUMENTS

| | | |
|---|---|---|
| 2003/0206949 A1 | 11/2003 | Parikh et al. |
| 2010/0003332 A1 | 1/2010 | Bae et al. |

FOREIGN PATENT DOCUMENTS

| | | |
|---|---|---|
| JP | 04-295420 A | 10/1992 |
| JP | 2006-089386 A | 4/2006 |
| WO | 2008/126797 A1 | 10/2008 |
| WO | 2010/032434 A1 | 3/2010 |
| WO | 2011/118960 A2 | 9/2011 |

OTHER PUBLICATIONS

Macinhe translation for WO 2011/118960; downloaded Dec. 16, 2014.*
Machine translation for WO 2008/126797; downloaded Dec. 16, 2014.*
PCT/JP2013/003023—International Search Report mailed on Jul. 16, 2013, in Japanese language.
European Search Report issued on Nov. 23, 2015, that issued in the corresponding European Patent Application No. 13787260.2.

* cited by examiner

*Primary Examiner* — Jeffrey T Palenik
(74) *Attorney, Agent, or Firm* — Cowan, Liebowitz & Latman, P.C.; Mark Montague

(57) ABSTRACT

An organic compound nano-powder comprising a granular organic compound with an average particle diameter of 500 nm or less and a 90%-diameter of less than 1500 nm and a carbohydrate compound comprising at least any one of a sugar and a sugar alcohol and with amount of 0.3 times or more by mass relative to amount of the organic compound, a method for producing the same, and a suspension having the organic compound dispersed in a liquid dispersion medium in which the organic compound is insoluble or poorly soluble.

10 Claims, No Drawings

ORGANIC COMPOUND NANO-POWDER, METHOD FOR PRODUCING THE SAME AND SUSPENSION

CROSS REFERENCE TO RELATED APPLICATION

The present patent application claims priority from Japanese Patent Application No. 2012-108972 filed in Japan on May 11, 2012, and the disclosures of thereof are incorporated herein by reference. In addition, the disclosures of the patents, patent applications and documents cited in the present application are incorporated herein by reference.

TECHNICAL FIELD

The present invention relates to an organic compound nano-powder, a method for producing the same, and a suspension having an organic compound dispersed therein.

BACKGROUND ART

In order to fulfill an inherent function of an active ingredient contained in a formulation or a health food without excessively taking it, it is necessary to enhance the bioavailability for the formulation or the health food. Taking the formulation as an example, while an oral formulation has the advantages of being convenient and causing little distress compared to an injectable formulation, it has the disadvantage of providing low bioavailability. The oral formulation enters into the intestine via the stomach and the duodenum, is absorbed into blood mainly through the intestinal tract and then is delivered to the liver via the portal vein. A part of the oral formulation is decomposed by undergoing the action of a gastric acid or the like or being metabolized in the liver during passing through such a long path, whereby converted into a totally different substance. One of the major reasons for the low bioavailability is that the oral formulation is difficult to be absorbed from digestive organs like the intestine. In order to enhance the bioavailability for the formulation, it is necessary to get the size down of the organic compound with medicinal ingredients to a level required to facilitate the absorption of the compound from the digestive organs into the blood.

In the case of the injectable formulation, a typical example of parenteral formulations, effective functioning of a medicinal ingredient in the formulation requires the reaching of the medicinal ingredient through blood vessels in the body to a target site. The inner diameter of a capillary blood vessel, which is the narrowest among the blood vessels, is about 5 μm. Accordingly, in order to make pass the organic compound with the medicinal ingredient through the capillary blood vessel without causing occlusion, the particle diameter of this organic compound needs to be 5 μm or less. Further, for the same reason as the oral formulation, it is necessary for a health food to get the size down of the organic compound with active ingredients to a level required to facilitate the absorption of the compound from the digestive organs into the blood.

In the case of a solid skin-lightening ingredient and a moisturizing ingredient contained in a cosmetic, less agglomeration and the smaller particle size are required in order to make them easily attached and thinly spread on a skin surface while if it is in the form of a milky lotion, not to cause phase separation in a container in which this cosmetic is contained so that a uniform dispersion state may be sustainable.

In accordance with recent development of a nanotechnology, the preparation of the nano-sized organic compound to satisfy the requirements as mentioned above has attracted high attention. For example, a particulate formulation which contains a steroid or a steroid derivative with median of the particle distribution in the range of 0.005 to 5 μm and with the 90%-diameter of 10 μm or less has been known (for example, see Patent Document 1). However, the coarse particles present with a small percentage in the particulate formulation due to so wideness of the particle diameter distribution causes a problem of instability of a suspension thereof, i.e., a problem of low dispersivity of the particulate formulation.

For example, as one of methods for finely-milling the organic compound to the level of nano-powder with a narrow particle diameter distribution, a method for milling the organic compound by a bead mill using beads made of ceramic, glass, or the like is well known (for example, see Patent Document 2). Nano-powder with a narrow particle diameter distribution can be obtained by applying such a mechanical impact or a grinding force to the particles of the organic compound. In addition, a wet milling method for milling the organic compound in organic liquid using salt particles as a milling medium is also known (for example, see Patent Documents 3 and 4). The method using salt particles is more advantageous than the method using the beads in view of less contamination with impurities coming from a milling medium. While the impurities coming from the beads are difficult to remove, the impurities coming from the salt particles are easy to remove by a water-washing process (also called salt-removing process) due to high water solubility of salt.

PRIOR ART PUBLICATIONS

Patent Documents

Patent Document 1: Japanese Patent Laid-Open Publication No. 2006-089386
Patent Document 2: Japanese Patent Laid-Open Publication No. H04-295420
Patent Document 3: International Publication WO/2008/126797
Patent Document 4: International Publication WO/2010/032434

SUMMARY OF INVENTION

Problem to be Solved by the Inventions

The wet milling method using the salt particles as milling medium is advantageous in view of avoiding contamination of irremovable impurities, but needs furthermore improvements. One of the improvements is to perform the production process as simple as possible with no water-washing to remove the salt that contaminates an organic compound after milling. When the salt particles are used as milling medium, usually the salt with the amount of preferably 10 to 30 times by mass relative to the organic compound to be milled is served into a wet milling apparatus. Unless thus large amount of salt is not removed after milling, the organic compound after milling cannot be safely used in or on a living body. Another of improvements is to prevent the wet milling apparatus from rusting out. Contamination due to rust must be definitely avoided when the organic compound is used in a living body. Use of an anti-rust agent as a general anti-rusting method is also well known, but contact thereof with the organic compound is not also allowed. Alternatively, a wet milling apparatus which is constructed by a material difficult to rust (for example, a personally-ordered apparatus which is coated with a ceramic on its inner surface) may be opted, but the apparatus is disadvantageous in view of high cost due to use of a special apparatus.

The present invention was made to satisfy the requirements as mentioned above and has an object to provide an organic compound nano-powder conveniently, with low cost and with less contamination of impurities to be removed.

Means for Solving the Problem

The inventors of the present invention carried out an extensive investigation to solve the problems mentioned above, and as a result, found that, when an organic compound having a granular form was milled by adding at least a granular carbohydrate compound (or sugar compound), the organic compound could be milled efficiently, and in addition, a salt removing process after milling became unnecessary, as well as rusting of a wet milling apparatus could be avoidable, and based on these findings, the present invention could be accomplished. Alternatively, there may be some cases that salt is optionally added to the granular carbohydrate compound, in this case, because the amount of the salt was incomparably smaller than the amount in case of being used as a milling medium, it was found that not only the salt removing process was unnecessary but also the risk of the rust of the wet milling apparatus could be reduced. Specific content of the present invention is as following.

One embodiment according to the present invention is an organic compound nano-powder comprising:

a granular organic compound with an average particle diameter of 500 nm or less and a 90%-diameter of less than 1500 nm; and a carbohydrate compound comprising at least any one of a sugar and a sugar alcohol and with amount of 0.3 times or more by mass relative to amount of the organic compound.

Other embodiment according to the present invention is the organic compound nano-powder, wherein the carbohydrate compound is in an amount of 0.5 to 30 times by mass relative to amount of the organic compound.

Further other embodiment according to the present invention is the organic compound nano-powder further comprising a physiologically acceptable polyol.

Further other embodiment according to the present invention is the organic compound nano-powder, wherein the carbohydrate compound are one or more kinds selected from the group consisting of mannitol, maltitol, xylitol, erythritol, glucose, fructose, inositol, lactose, trehalose, cellobiose and dextrin.

Further other embodiment according to the present invention is the organic compound nano-powder further comprising a physiologically acceptable salt.

Further other embodiment according to the present invention is the organic compound nano-powder, wherein the physiologically acceptable salt is sodium chloride.

Still further other embodiment according to the present invention is the organic compound nano-powder, wherein the organic compound is one or more kinds selected from the group consisting of clarithromycin, fexofenadine hydrochloride, fluorometholone, curcuminoid, curcumin, rutin, mefenamic acid, acetaminophen, ibuprofen, amphotericin B, diclofenac sodium, indomethacin, felbinac, pranlukast hydrate, dexamethasone and fenofibrate.

One embodiment according to the present invention is a suspension having at least an organic compound, which is contained in the organic compound nano-powder according to any one of the above-mentioned, dispersed in a liquid dispersion medium in which the organic compound is insoluble or poorly soluble.

One embodiment according to the present invention is a method for producing an organic compound nano-powder comprising:

mixing a granular organic compound, a granular carbohydrate compound comprising at least any one of a sugar and a sugar alcohol and with amount of 0.3 times or more by mass relative to amount of the organic compound, and liquid in which the organic compound is insoluble or poorly soluble; and wet-milling the organic compound after the mixing so that an average particle diameter thereof becomes 500 nm or less and a 90%-diameter thereof becomes less than 1500 nm.

Other embodiment according to the present invention is the method for producing an organic compound nano-powder, wherein the carbohydrate compound is in an amount of 0.5 to 30 times by mass relative to amount of the organic compound.

Further other embodiment according to the present invention is the method for producing an organic compound nano-powder, wherein the mixing is carried out with adding a physiologically acceptable polyol as liquid in which the organic compound is insoluble or poorly soluble.

Further other embodiment according to the present invention is the method for producing an organic compound nano-powder, wherein the wet-milling of the organic compound is carried out while kneading the mixture obtained after the mixing in a kneader.

Further other embodiment according to the present invention is the method for producing an organic compound nano-powder, wherein a process of drying is carried out after the milling.

Further other embodiment according to the present invention is the method for producing an organic compound nano-powder, wherein the carbohydrate compound are one or more kinds selected from the group consisting of mannitol, maltitol, xylitol, erythritol, glucose, fructose, inositol, lactose, trehalose, cellobiose and dextrin.

Further other embodiment according to the present invention is the method for producing an organic compound nano-powder, wherein a physiologically acceptable salt is further mixed in the process of the mixing.

Further other embodiment according to the present invention is the method for producing an organic compound nano-powder, wherein the physiologically acceptable salt is sodium chloride.

Still further other embodiment according to the present invention is the method for producing an organic compound nano-powder, wherein the organic compound are one or more kinds selected from the group consisting of clarithromycin, fexofenadine hydrochloride, fluorometholone, curcuminoid, curcumin, rutin, mefenamic acid, acetaminophen, ibuprofen, amphotericin B, diclofenac sodium, indomethacin, felbinac, pranlukast hydrate, dexamethasone and fenofibrate.

Advantageous Effect of the Invention

According to the present invention, an organic compound nano-powder can be provided conveniently, with low cost and with less contamination of impurities to be removed.

DESCRIPTION OF EMBODIMENTS

Next, the embodiments of the organic compound nano-powder, the method for producing the same, and the suspension according to the present invention will be described.

1. Organic Compound Nano-Powder

The organic compound nano-powder according to the embodiment comprises:

a granular organic compound (A) with an average particle diameter of 500 nm or less and a 90%-diameter of less than 1500 nm; and a carbohydrate compound (B) comprising at least any one of a sugar and a sugar alcohol and with amount of 0.3 times or more by mass relative to amount of the organic compound.

The organic compound nano-powder may further comprise a physiologically acceptable salt (C).

Alternatively, the organic compound nano-powder may further comprise, in accordance with its use, one or more additives (D) other than the salt.

The term "average particle diameter" used in present specification means a mathematical average diameter (here, defined as the $D_{av}$ value) in the particle diameter distribution as measured by a dynamic light scattering photon correlation method. The term "50%-diameter" (defined as median diameter or the $D_{50}$ value) means a certain particle diameter when amount of a larger side becomes equal to amount of a smaller side of the particle diameters divided into two a powder from the certain particle diameter. The term "90%-diameter" ($D_{90}$ value) means the particle diameter of the particle at the position of 90% when counted from the smallest size zero (minimum) to 100% (maximum) of the particle diameter in the particle diameter distribution as measured by the above-mentioned measurement method. The term "10%-diameter" ($D_{10}$ value) means the particle diameter of the particle at the position of 10% when counted from the smallest size zero (minimum) to 100% (maximum) of the particle diameter in the particle diameter distribution as measured by the above-mentioned measurement method. The average particle diameter of the organic compound is more preferably in the range of 50 to 400 nm, further more preferably in the range of 100 to 350 nm. The $D_{90}$ value of the organic compound is more preferably less than 700 nm, further more preferably less than 500 nm.

"Organic compound nano-powder" in the present specification may be any powder so far as the powder contains at least an organic compound (A) having a granular form and a carbohydrate compound (B); and thus, one or more additives other than these compounds may be contained therein. The particle diameter distribution by the dynamic light scattering photon correlation method is measured for the organic compound having a granular form. However, if the carbohydrate compound is physically attached or chemically bonded to the surface of the particles of the organic compound, the particle diameter distribution is measured for the granular organic compound having this carbohydrate compound attached or bonded thereto.

(A) Organic Compound

The organic compound includes those used as active ingredients in a medicine, a health food, a nutritional supplement, a cosmetic and the like, but is not limited to them. Preferable examples as the use for the medicine include an anti-obesity drug, a corticosteroid, an elastase inhibitor, an analgesics, an antifungal, a drug for cancer, an antiemetic, a cardiovascular drug, an anti-inflammatory drug, an anti-parasitic, an anti-arrhythmic, an antibiotic, an anticoagulant, an antidepressant, an anti-diabetic, an antiepileptic drug, an antihistamine, a hypotensive drug, an anti-muscarinic drug, an anti-mycobacteria drug, an antitumor drug, an immunosuppressant, an antithyroid, an antiviral, a sedative, a beta-adrenergic receptor antagonist, a blood product, a cardiac, a contrast medium, an antitussive, a diagnostic agent, a diagnostic contrast medium, a diuretic, a dopaminergic drug, a hemostatic, an immunizing drug, a lipid regulator, a musclerelaxant agent, a parasympathomimetic drug, a parathyroid calcitonin and its diphosphonate salt, a prostaglandin, a radioactive drug, a sex hormone, an anti-allergic drug, a stimulant, an appetite-suppressant, a sympathomimetic drug, a thyroid drug, a vasodilator, an anti-parkinson drug, a psychotropic agent, an agent affecting the central nervous system, an antipyretic, an anti-anxiety drug and a hypnotic. However, the medicines are not limited to the above examples.

Specific examples of the organic compound used for the medicines include 5-fluorourasil, 7-(3,5-dimethoxy-4-hydroxycinnamoylamino)-3-octyloxy-4-hydroxy-1-methyl-2 (1H)-quinoli none, acarbose, aciclovir, acetyl salicylic acid, acetyl pheneturide, acetaminophen, adenine, atenolol, opium alkaloid, amidotrizoic acid, amphotericin B, amoxapine, amobarbital, amurine, amoxicillin, aripiprazole, alprazolam, allopurinol, ampicillin, ampiroxicam, amlexanox, isoproterenol, ibuprofen, ipriflavone, imipramine, irbesartan, indomethacin, ubenimex, urapidil, ursodesoxycholic acid, estazolam, estradiol, etizolam, ethenzamide, ethotoin, enoxacin, eprosartan, emiglitate, erythromycin, prazosin hydrochloride, propafenone hydrochloride, entacapone, oxazolam, oxaprozin, oxycodone, oxytetracycline, oxypertine, oxendolone, omeprazole, olanzapine, oryzanol, caffeine, captopril, cabergoline, carbamazepine, chlorphenesin carbamate, carpipramine maleate, carbochromen, carumonam sodium, candesartan cilexetil, quazepam, guanfacine, sildenafil citrate, clarithromycin, griseofulvin, cloxazolam, clozapine, clotiazepam, clonazepam, clobazam, chloramphenicol, chlordiazepoxide, chlorzoxazone, chlortalidone, chlorpheniramine, chlorpromazine, chlorhexidine, ketoprofen, cocaine, codeine, colchicine, chlormadinone acetate, cortisone acetate, saccharin, zafirlukast, salazosulfapyridine, salbutamol, diastase, diazepam, digitoxin, ciclacillin, diclofenac sodium, digoxin, disopyramide, citicoline, dihydrocholesterol, dipyridamole, dihydrocodeine, difenidol, diphenhydramine, cimetidine, dimenhydrinate, cilostazol, simvastatin, scopolamine, stanozolol, sparfloxacin spiperone, spironolactone, sulindac, sulpiride, sulbenicillin sodium, cephalexin, cefixime, cefozopran, cefotiam, cefsulodin sodium, cefinenoxime, seratrodast, serrapeptase, celecoxib, zotepine, zonisamide, zopiclone, dacarbazine, tacrolimus hydrate, tasosartan, danazol, dantrolene sodium, tiaprofen, timidazole, timiperone, theophylline, dexamethasone, dextromethorphan, delapril, terguride, telmisartan, ipecac, tofisopam, trandolapril, triazolam, triamcinolone, triamcinolone acetonide, triamterene, tolbutamide, trepibutone, troglitazone, droperidol, naproxen, nalidixic acid, nicardipine, nicergoline, nitrazepam, nifedipine, nimetazepam, nimodipine, nemonapride, noscapine, paclitaxel, papaverine, valsartan, haloperidol, pioglitazone, bicalutamide, bisbentiamine, hydralazine, hydroxyzine pamoate, pivmecillinam, biperiden, pimozide, pirenoxine, piroxicam, pindolol, famotidine, falecalcitriol, fexofenadine hydrochloride, phenacemide, phenyloin, phenylephrine, phenobarbital sodium, fenofibrate, felbinac, phenprobamate, forasartan, bucolome, budesonide, clemastine fumarate, formoterol fumarate, pranoprofen, pravastatin, pranlukast hydrate, primidone, fludiazepam, flunitrazepam, proglumetacin maleate, blonanserin, profenamine hibenzate, bromazepam, flutazolam, fluocinolone acetonide, fluorometholone, fluconazole, flutoprazepam, flunisolide, fluphenazine decanoate, flufenamic acid aluminum, flumazenil, flurbiprofen, prednisolone, procainamide, furosemide, brotizolam, fluticasone propionate, beclomethasone propionate, propranolol, propericiazine, promethazine, bromperidol, bromocriptine mesilate, beta-carotene, betamethasone, verapamil, benzthiazide, pentazocine, voglibose, propyl gallate, polythiazid, mitomycin C, mazindol, manidipine, maprotiline, maltol, lisuride maleate, miglitol, miconazole, midazolam, minoxidil, milrinone, mexazolam, mequitazine, meclizine, meclofenoxate, medazepam, methylephedrine, methyldopa, methocarbamol, metoclopramide, methotrexate, mefenamic acid, meloxicam, modafinil, mofezolac, molsidomine, folic acid, ranitidine, labetalol, rabeprazole, ramelteon, lansoprazole, liothyronine sodium, risperidone, lysozyme, lidocaine, rifampicin, leuprorelin, reserpine, levallorphan, L-dopa, riluzole, losartan, lofepramine hydrochloride, lorazepam and lormetazepam. However, the organic compound is not limited to these compounds. Especially, clarithromycin, fexofenadine hydrochloride and fluorometholone are preferably used in the above organic compounds.

Examples of the organic compound used for health food or nutritional supplement include astaxanthin, alliin, allysine, anthocyanin, isoflavone, isorhamnetin, α-lipoic acid, oleuropein, ornithine, catechin, capsaicin, capsanthin, capsorubin, beta-carotene, carnitine, carminic acid, canthaxanthin, ginkgolide, glucan, chitosan, quinone, gymnemic acid, beta-cryptoxanthin, curcuminoids, curcumin, glucosamin, creatine, chlorophyll, quercetin, sesame lignan, zeaxanthin, bixin, biotin, vitamin A and its derivative, vitamin D2, vitamin D3, phytosterol, phosphatidylserine, beta-apo-4-carotenal, ethyl beta-apo-8-carotenoate, flavonoid, proanthocyanidin, pectin, polyphenol, monacolin K, ubiquinone, lycopene, resveratrol, lutein and rutin. However, the organic compound is not limited to these compounds. Especially, curcuminoid, curcumin and rutin are preferably used in the above organic compounds.

Examples of the cosmetic include an anti-aging agent, a UV-screening material, a tightening-up agent, an antioxidant, an anti-wrinkling material, a moistening agent, a blood circulation promoter, an antibacterial agent, a disinfecting agent, a drying agent, a cooling agent, a warming agent, vitamins, amino acids, a wound-heal acceleration agent, an irritation relaxation agent, a painkiller, a cellular stimulant and various enzymes. However, the cosmetic is not limited to these examples.

Examples of the organic compound used for these cosmetics include 4-n-butyl resorcinol, N-acylated glutathione, ascorbic acid, ascorbic acid salt, ascorbic acid glucoside, magnesium ascorbyl phosphate, arbutin, isoferulic acid, isoferulic acid salt, ellagic acid, ergo acid, ergo acid salt, kinetin, casein, caffeic acid, caffeic acid salt, glabridin, glycyrrhizic acid, glutathione, glutathione ester, glutathione salt, kojic acid, retinol acetate, cysteine, tannic acid, tranexamic acid, transferrin, tretinoin, hydroquinone, hydroquinone salt, phytic acid, fibrin, fibroin, fibronectin, ferulic acid, ferulic acid salt, lycopene, retinyl acetate, retinyl palmitate, retinol, retinoic acid and retinoic acid tocopheryl. However, the organic compound is not limited to these compounds.

(B) Carbohydrate Compound

The carbohydrate compound includes at least one kind selected from the group consisting of sugars (monosaccharide, disaccharide, polysaccharides including trisaccharide and higher than trisaccharide, and oligosaccharides) and sugar alcohols. The carbohydrate compound is selected such that it may not be overlapped with the foregoing organic compounds.

Examples of the monosaccharide include glucose, galactose, mannose, fructose, inositol, ribose and xylose. Examples of the disaccharide include lactose, sucrose, cellobiose, trehalose and maltose. Examples of the polysaccharide include pullulan, sodium hyaluronate, raffinose, melezitose, sodium chondroitin sulfate, cellulose, cluster dextrin, cyclodextrin, dextrin, dextran, xanthan gum, chitin and chitosan. Examples of the oligosaccharide include fructo oligosaccharide, galacto oligosaccharide, mannan oligosaccharide, gentio oligosaccharide, xylo oligosaccharide, cello oligosaccharide, isomalto oligosaccharide, nigero oligosaccharide, chito oligosaccharide, fucoidan oligosaccharide, soy bean oligosaccharide and lactosucrose. Examples of the sugar alcohol include palatinose, sorbitol, lactitol, erythritol, pentaerythritol, xylitol, maltitol, mannitol and dulcitol. In this embodiment, sugar alcohols, monosaccharide or disaccharide may be preferably used as the carbohydrate compound, while mannitol, maltitol, erythritol, xylitol, glucose, fructose, lactose, trehalose or cellobiose may be used more preferably, and D-mannitol, xylitol, glucose, fructose or trehalose may be used further more preferably.

In the organic compound nano-powder, the carbohydrate compound may be contained in the form of particles independent of particles of the organic compound or may be in the form physically attached or chemically bonded to the surface of particles of the organic compound.

The carbohydrate compound is contained in the organic compound nano-powder with the amount of 0.3 times or more, preferably 0.3 to 100 times, more preferably 0.5 to 30 times, or further more preferably 0.8 to 20 times by mass relative to the organic compound. For the purpose of no excess exclusion of the carbohydrate compounds after milling the organic compound and the inhibition of excessively high osmotic pressure of liquid including the carbohydrate compounds at using the liquid due to inclusion of excess amount of the carbohydrate compounds in the liquid, the additive amount of the carbohydrate compounds is preferably 0.3 to 100 times, more preferably 0.5 to 30 times, further preferably 0.8 to 20 times, still further preferably 1 to 8 times by mass relative to the organic compound. Above-mentioned carbohydrate compounds may be used singly or as a mixture of two or more of them. In addition, the carbohydrate compounds may be used in the form of fine particles.

The carbohydrate compound can function as a milling medium or as an auxiliary agent for milling during milling the organic compound. Here, the term "milling medium" means a medium which directly applies an impact or a grinding action to the organic compound. The term "auxiliary agent" means a material which does not directly apply above actions to the organic compound but facilitates the milling of the organic compound by working indirectly. Further, the carbohydrate compound can work to reduce agglomeration among particles of the organic compound.

(C) Physiologically Acceptable Salt

The salt that can be mixed with the organic compound nano-powder of this embodiment is one that can be used without notably causing a physiological problem. In other words, the salt is not particularly limited as far as it does not pose a significant problem even if it enters into a living body or contacts to a skin. A physiologically acceptable salt preferably has sufficient hardness to finely mill the organic compound. In addition, the amount of the physiologically acceptable salt mixed with the organic compounds and the carbohydrate compounds means such amount of the salt that the salt does not bring critical matters to a biological body when it is consumed in the biological body.

Examples of the preferable salt include sodium chloride, potassium chloride, ammonium chloride, sodium sulfate, magnesium sulfate, potassium sulfate, calcium sulfate, sodium malate, sodium citrate, disodium citrate, sodium dihydrogen citrate, potassium dihydrogen citrate, sodium dihydrogen phosphate, potassium dihydrogen phosphate, disodium hydrogen phosphate and dipotassium hydrogen phosphate. More preferable examples of the salt include sodium chloride, potassium chloride, magnesium sulfate, calcium sulfate, sodium citrate, sodium dihydrogen phosphate, potassium dihydrogen phosphate, disodium hydrogen phosphate and dipotassium hydrogen phosphate and most preferable salt is sodium chloride.

The salt may be adjusted in its particle diameter by milling and the like before it is mixed with the organic compound or the carbohydrate compound. In the case of preliminary adjustment of the particle diameter, the average particle diameter of the salt is preferably 0.01 to 300 μm, more preferably 0.1 to 100 μm or further more preferably 0.5 to 50 μm. Amount of the salt contained in the organic compound nano-powder may be in the range of 0.02 to 4 times by mass, preferably 0.05 to 2 times by mass, or more preferably 0.1 to 1.5 times by mass, relative to total amount of the organic compound and the carbohydrate compound. The salts may be used singly or as a mixture of two or more of them. The salt can function as a milling medium or as an auxiliary agent for milling during the milling of the organic compound.

(D) Other Additives

The organic compound nano-powder may contain all or a part of viscosity modifier added during the manufacturing thereof. A physiologically acceptable polyol may be preferably used as the viscosity modifier. The term "physiologically acceptable" has the same meaning as the term "physiologically acceptable" of the physiologically acceptable salt mentioned above. Examples of the physiologically acceptable polyol include glycerin, propylene glycol, polyethylene glycol, dipropylene glycol, ethylene glycol, diethylene glycol, citric acid, DL-malic acid, tartaric acid, lactic acid, urea, maleic acid and malonic acid, and preferably citric acid, propylene glycol and glycerin. These viscosity modifiers may be used singly or as a mixture of two or more of them.

The organic compound nano-powder tends to agglomerate very easily because individual particles thereof are in the level of nano-size. The organic compound nano-powder may keep containing all or a part of anti-agglomeration agent added during or after milling in order to prevent the particles of the organic compound nano-powder from agglutinating. Examples of the anti-agglomeration agent include ethanol, glycerin, propylene glycol, sodium citrate, purified soy bean lecithin, phospholipid, D-sorbitol, lactose, xylitol, Gum arabic, sucrose fatty acid ester, sodium dodecylsulfate, polyoxyethylene hydrogenated castor oil, polyoxyethylene fatty acid ester, polyoxyethylene glycol, polyoxyethylene sorbitan fatty acid ester, alkylsulfate salt, alkylbenzenesulfonate, sulfosuccinate salt, polyoxyethylene polyoxypropylene glycol, polyvinyl pyrrolidone, polyvinyl alcohol, hydroxypropyl cellulose, methyl cellulose, hydroxyethyl cellulose, hydroxypropyl methyl cellulose, sodium carmellose, sodium carboxymethyl cellulose, carboxymethyl polymer, N-acyl-glutamate salt, acrylic acid copolymer, sodium myristoylmethyl taurine, polyoxyl stearate, carboxyvinyl polymer, sodium dioctyl sulfosuccinate, xanthan gum, methacrylic acid copolymer, casein sodium, L-valine, L-leucine, L-isoleucine, benzarconium chloride and benzethonium chloride. The anti-agglomeration agents may be preferably glycerin, sucrose fatty acid ester, sodium dodecylsulfate, polyvinyl pyrrolidone, polyvinyl alcohol, hydroxypropyl cellulose, sodium carboxymethyl cellulose, sodium myristoylmethyl taurine, polyoxyl stearate, carboxyvinyl polymer, sodium dioctyl sulfosuccinate and xanthan gum. Above anti-agglomeration agents may be used singly or as a mixture of two or more of them. Meanwhile, above-mentioned other additives are selected such that they may not overlap with the organic compound, the carbohydrate compound and the salt.

2. Suspension Dispersed Organic Compound Nano-Powder

The suspension according to the embodiment of the present invention comprises the organic compound (A) in liquid dispersing medium in which the organic compound is insoluble or poorly soluble.

The term "insoluble or poorly soluble" used in the present specification means that solubility of the organic compound in the liquid dispersing medium is 10 mg/mL or less, or preferably 1 mg/mL or less, at the temperature of a normal operation, for example, at room temperature of around 25 degrees C. The liquid dispersing medium in which the organic compound is insoluble or poorly soluble may include water; organic solvent like ethanol; or polyol like glycerin, propylene glycol, polyethylene glycol, ethylene glycol, diethylene glycol. However, the liquid dispersing mediums are not limited to above-exemplified some liquids and may be any kinds of mediums as long as the mediums are in the form of liquid at room temperature of around 25 degrees C. Thus, for example, when polyol is used as the liquid dispersing medium, the polyol may also operate as a viscosity modifier or an anti-agglomeration agent. For example, when the organic compound is water-soluble, the liquid dispersing medium in which the organic compound is insoluble or poorly soluble means one other than water. Further, when the organic compound is soluble in a certain organic solvent, the liquid dispersing medium means one other than the certain organic solvent. In other words, the liquid dispersing medium needs to be selected such that the organic compound may exist in the dispersed state without being completely dissolved therein. When the suspension is used as it is as a medicine, a health food, or a cosmetic, the dispersing medium including mainly water is preferably used.

The suspension according to the present embodiment may contain various viscosity modifiers and anti-agglomeration agents mentioned in the section of other additives (D), and may further contain an emulsifying agent, a pH modifier, a buffering agent, a preservative or the like. Examples of the materials that may be contained in this suspension include: phosphate salts such as sodium dihydrogen phosphate, disodium hydrogen phosphate, trisodium phosphate, sodium pyrophosphate, sodium tripolyphosphate, sodium tetrapolyphosphate, sodium hexametaphosphate, acidic sodium hexametaphosphate and potassium dihydrogen phosphate; hydrates of these salts; sodium edetate; and sodium hydroxide.

3. Method for Producing the Organic Compound Nano-Powder

The method for producing an organic compound nano-powder according to the present embodiment comprises:

(A) a process of mixing a granular organic compound, a granular carbohydrate compound comprising at least any one of a sugar and a sugar alcohol and with amount of 0.3 times or more by mass relative to amount of the organic compound, and liquid in which the organic compound is insoluble or poorly soluble; and (B) a process of wet-milling the organic compound until an average particle diameter thereof becomes 500 nm or less and a 90%-diameter thereof becomes less than 1500 nm after the process of mixing.

The method for producing an organic compound nano-powder may further comprise (C) a process of drying the product after (B) the process of milling. In the following, "a process of mixing", "a process of milling" and "a process of drying" will be explained.

(A) Process of Mixing

The method for producing the organic compound nano-powder includes the process of mixing at least a granular organic compound, a granular carbohydrate compound and liquid in which the organic compound is not soluble or poorly soluble. The process of mixing may be done by adding one or more additives other than above materials (such as an anti-agglomeration agent, a viscosity modifier, a pH-modifier). The process of mixing has a feature that the granular carbohydrate compound is added to the granular organic compound with the amount of 0.3 times or more by mass relative to the organic compound. When the milling is performed by adding the carbohydrate compound with the amount of 0.3 times or more by mass relative to the organic compound, the organic compound may be milled more finely. The organic compound may be milled finely even if the carbohydrate compound is added more excessively than 0.3 times by mass relative to the organic compound. However, in this case, it is needed to decrease the amount of the organic compound to enter in a milling apparatus, thus the amount of the organic compound produced per one process of the milling decreases. For the purpose of producing organic compound fine particles more than a certain amount and milling the organic compound more finely, the amount of the carbohydrate compound to enter in the milling apparatus is preferably 0.3 to 100 times, more preferably 0.5 to 30 times, further more preferably 0.8 to 20 times, or still further preferably 1 to 8 times by mass relative to the organic compound.

The carbohydrate compound has a function as the anti-agglomeration agent. But, if the carbohydrate compound is added only to work this function, addition of the carbohydrate compound "in the granular form" with the amount of "0.3 times or more by mass relative to the organic compound" is not necessary as its condition. The reason why the carbohydrate compound is added "in the granular form" with the amount of "0.3 times or more by mass relative to the organic compound" is as follows. It is necessary to work the function of a milling medium that provides an impact or a grinding action directly with the granular organic compound or the function of a milling auxiliary agent that indirectly relates to facilitate collision and grinding among the granular organic compound by themselves.

Various kinds of sugars and sugar alcohols already explained in the section of the organic compound nano-powder, including a mixture of two or more of them may be used as the granular carbohydrate compound. Especially, sugar alcohols, monosaccharide or disaccharide may be preferably used as the carbohydrate compound, while mannitol, maltitol, erythritol, xylitol, glucose, fructose, lactose, trehalose or cellobiose may be used more preferably, and D-mannitol, xylitol, glucose, fructose or trehalose may be used further more preferably. Although particle diameters of the granular carbohydrate compound may be selected in accordance with milling conditions, the average particle diameter of the carbohydrate compound is preferably in the range of 0.5 to 1000 μm, more preferably 1 to 700 μm or further more preferably 5 to 200 μm, in order to effectively make function as the milling medium or as the milling auxiliary agent.

In the process of mixing, a physiologically acceptable salt may be additionally mixed. In this case, for example, amount of the physiologically acceptable salt to be mixed is preferably 0.02 to 4 times by mass relative to total amount of the organic compound and the carbohydrate compound. As long as above-mentioned amount of the salt is mixed with the organic compound and the carbohydrate compound, it is not necessary to remove the salt and it is also possible to reduce the rusting of a milling apparatus. Various salts already explained in the section of the organic compound nano-powder may be used as the salt. Especially, sodium chloride is preferably used. Although various particle diameters of granular salts may be selected, for example, from the range of preferably 0.01 to 300 μm, more preferably 0.1 to 100 μm or further more preferably 0.5 to 50 μm.

The liquid in which the organic compound is insoluble or poorly soluble means that solubility of the organic compound in the liquid is 10 mg/mL or less, or preferably 1 mg/mL or less, at the temperature of a normal operation, for example, at room temperature of around 25 degrees C. The liquid dispersing medium in which the organic compound is insoluble or poorly soluble may include water; organic solvent like ethanol; or polyol like glycerin, propylene glycol, polyethylene glycol, ethylene glycol, diethylene glycol. However, the liquid is not limited to above-exemplified liquid and may be any kinds of liquid as long as it is in the form of liquid at room temperature of around 25 degrees C. When polyol is used as the liquid, the polyol may also operate as a viscosity modifier or an anti-agglomeration agent. For example, when the organic compound is water-soluble, the liquid in which the organic compound is insoluble or poorly soluble means one other than water. Further, when the organic compound is soluble in a certain organic solvent, the liquid means one other than the certain organic solvent. In other words, the liquid is selected such that the organic compound may exist in the state without being completely dissolved therein in the process of mixing and the process of milling after the mixing.

The process of mixing may be performed before the milling or simultaneously with the milling in a milling apparatus used in the process of milling that will be explained later, or may be performed in a mixing vessel prepared as the apparatus different from the milling apparatus. In the latter case, the mixing may be performed by using an agitating machine wherein a mixing blade is rotated, a magnetic stirrer wherein a stirring chip is rotated by using a magnetic force in a vessel, a vibration mill wherein a vessel is moved up and down, a bath wherein an ultrasonic wave is oscillated and the like.

(B) A Process of Milling

In the method for producing the organic compound nano-powder according to the present embodiment, the milling apparatus usable for wet milling of the organic compound is not particularly limited as far as the apparatus is capable of milling the organic compound finely by mechanical means. Examples of the milling apparatus include any convenient milling apparatuses such as a kneader, a twin roll mill, a triple roll mill, a fret mill, a Hoover Muller mill, a disk blade kneader and a biaxial extruder. The significant feature of the process of milling is no use of milling media like balls and beads. In a prior milling method in which the organic compound to be milled is entered with balls or beads into the milling apparatus, the organic compound is contaminated by abrasion particles coming from the balls or beads, whereby removal of the contaminants is impossible or requires tremendous work and cost even if removal thereof may be theoretically possible. To eliminate such a demerit in the prior methods, in the process of milling, a milling apparatus giving a force only to knead the compound to be milled is used so that the organic compound may be finely milled by utilizing an impact or a grinding action applied among the particles of the organic compound themselves or between the particles of the organic compound and the carbohydrate compound. With the basis of such a technical concept, among the milling apparatuses mentioned above, a disk blade kneader which can generate a strong kneading force by a planetary motion of a blade is preferably used. In this case, the process of milling is performed by the milling the organic compound while kneading in the kneader the mixture after the process of mixing.

In the process of milling the organic compound, the milling may be done, after the organic compound, the carbohydrate compound and a small amount of the liquid are all entered into the milling apparatus, or be done with adding the carbohydrate compound and/or the liquid little by little. Temperature at the milling may be determined arbitrarily in considering the organic compound to be milled, the milling apparatus and the like. The temperature is not particularly limited as far as it can inhibit melting or decomposition of the organic compound, is preferably −50 to 50 degrees C., more preferably −20 to 30 degrees C., or at most preferably −10 to 25 degrees C. Time for milling may be determined arbitrarily in considering the organic compound to be milled, the milling apparatus and the like. Time for milling is, for example, about 1 to 50 hours, preferably 2 to 20 hours, or more preferably 3 to 10 hours.

(C) A Process of Drying

When a process of drying is carried out after the foregoing process of milling, the organic compound nano-powder may be obtained in the form of not a dispersion solution but a solid. Method for drying the milled product is not particularly limited. Thus, any convenient methods for drying the organic compound may be used. Examples of the drying method include a vacuum drying method, a freeze drying method, a spray drying method and a freeze spray drying method. Drying temperature, drying time and the like are not particularly limited. The drying may be carried out preferably at lower temperature to maintain chemical stability of individual particles that constitute the organic compound nano-powder and to prevent the particles from agglutinating secondarily. The vacuum drying method, the freeze drying method, the spray drying method and the freeze spray drying method are more preferable as the drying method.

(D) Other Process

The product obtained after the process of milling (the product is usually obtained in the form of "dough") may be taken out and then sent to the process of drying as it is, but it may also be subjected to a process of dispersion before the process of drying. For example, the process of drying may be preferably performed after agglomerated particles in the product obtained after the process of milling are dispersed into water (or an organic solvent) by using a dispersing machine like a magnetic stirrer, an ultrasonic disperser or a high pressure homogenizer.

4. Formulation

The organic compound nano-powder obtained by the method according to the present embodiment has excellent formulation properties so that the powder may be applied to various formulations. For example, when the powder is applied to an inhalant agent, the product obtained after the process of milling may be mixed with water to prepare a suspension. Then, the porous particles having the particle diameter of about 1 to 30 μm may be prepared by freeze spray drying of the suspension. To improve dispersing quality of the particles, small amount of surfactant may be added to above-mentioned water. Alternatively, for the same reason, small amount of volatile additive like ethanol may be added to the water. When the volatile additive is added, the additive can be removed during drying. Thus, an irritation may be lowered as compared with the case of adding a surfactant.

When the organic compound nano-powder is applied to an injectable formulation, an ophthalmic formulation, an ointment, a transdermal absorbing formulation and the like, a water-dispersion product may be prepared by adding an anti-agglomeration agent to the product obtained after the process of milling. For example, convenient surfactants may be used as the anti-agglomeration agents. Specifically, various anti-agglomeration agents mentioned in the section of the organic compound nano-powder may be used. A water-dispersion product using a polymer like an acrylic acid copolymer and a methacrylic acid copolymer, which is also the anti-agglomeration agent may be used as a DDS formulation. The water-dispersion product may be prepared by using a usually used machine. Examples of the machine include a homogenizer, a homomixer, an ultrasonic disperser and a high-pressure homogenizer.

The water-dispersion product may be made to powder by a vacuum drying, a spray drying, a freeze drying, a freeze spray drying or the like. The powder prepared by such a method has an excellent re-dispersing quality into water and thus is excellent for the applications to an injectable formulation, an ophthalmic formulation and an oral formulation to be prepared before use.

Alternatively, the organic compound nano-powder may be used for an ointment, a capsule formulation, a transdermal absorption formulation and the like by dispersing it into an oily substance. The oily substance is not particularly limited as far as it is usable in a usual formulation. Examples of the oily substance include liquid paraffin, vaseline, propylene glycol, glycerin, polyethylene glycol and a vegetable oil. The oily substances may be used singly or as a mixture of two or more of them. A dispersion product in the oily substance may be prepared by using a convenient machine. Examples of the machine include a homogenizer, a homomixer, an ultrasonic disperser, a high-pressure homogenizer, a twin roll mill, a triple roll mill, a disk blade kneader disperser and a biaxial extruder.

EXAMPLES

Next, Examples of the present invention will be explained. However, the present invention is not limited to the following Examples.

Experiment 1

Preparation of an Organic Compound Nano-Powder

Example 1

Preparation of Powder Containing 10% by Weight of Turmeric (1) Processes of Mixing and Milling 10 g of turmeric powder (>90% purity of curcuminoid, manufactured by Bio Actives Japan Corp.), 78 g of D-(−)-mannitol (particle diameter distribution in the range of 10 to 300 μm, manufactured by Wako Pure Chemical Industries, Ltd.), 10 g of a sucrose fatty acid ester (trade name of DK Ester SS, manufactured by Dai-Ichi Kogyo Seiyaku Co., Ltd.), 1.7 g of sodium carboxymethyl cellulose (trade name of Cellogen F-3H, manufactured by Dai-Ichi Kogyo Seiyaku Co., Ltd.) and 9 g of purified water were introduced into a 500-mL trimix kneader (manufactured by Inoue MFG, Inc.) and then were mixed and kneaded with keeping the load current of 0.95 to 1.2 A for about 3 hours. The particle diameter distribution of the turmeric powder measured before the process of mixing by the particle diameter distribution measurement instrument (instrument name of Delsa Nano, manufactured by Beckman Coulter Inc.) was as follows: the average particle diameter $(D_{av})$=12820 nm, the value of $D_{10}$=3793 nm, the value of $D_{50}$=10530 nm, and the value of $D_{90}$=25520 nm. A part (10 mg) of the kneaded product (referred as "dough") taken out after mixing and kneading was weighed into a 50-mL glass vial. After that, 10 mL of purified water was put into the glass vial, and then a mixture of the kneaded product and water was served to the dispersion treatment using a bath-type ultrasonic disperser (type of US100 III, manufactured by AS ONE Corp.) for 1 to 2 minutes. The particle diameter distribution of the kneaded product measured by the foregoing particle diameter distribution measurement instrument after the dispersion treatment was as follows: the average particle diameter ($D_{av}$)=202 nm, the value of $D_{10}$=78 nm, the value of $D_{50}$=162 nm, and the value of $D_{90}$=338 nm.

(2) A Process of Dispersion 54 g of purified water was added to above-mentioned dough (6 g). Then, a mixture of the dough and water was agitated by using a magnetic stirrer and then was served to the dispersion treatment using a probe-type ultrasonic disperser (probe-type 406 HWS with Amp. of 30 for 2 minutes, S4000 type, Astrason).

(3) A Process of Drying

Next, the dispersion solution obtained in the foregoing process of dispersion was served into a spray dryer (type of B-290, manufactured by Buchi Labortechnik AG, with flow of 45, inlet temperature of 150 degrees C., aspirator of 100%, and feed pump of 35%). As a result, 4.35 g of dry powder was obtained. A part (10 mg) of the obtained dry powder was mixed with 10 mL of purified water. Then, a mixture of the dry powder and water was served to the dispersion treatment using the foregoing bath-type ultrasonic disperser for 1 to 2 minutes. The particle diameter distribution of turmeric nano-powder measured by the foregoing particle diameter distribution measurement instrument after the dispersion treatment was as follows: the average particle diameter ($D_{av}$)=223 nm, the value of $D_{10}$=99 nm, the value of $D_{50}$=185 nm, and the value of $D_{90}$=336 nm.

Example 2

Preparation of Powder Containing 20% by Weight of Turmeric (1) Processes of Mixing and Milling 20 g of the turmeric powder used in Example 1, 65 g of the D-(−)-mannitol used in Example 1, 10 g of the sucrose fatty acid ester used in Example 1, 1.6 g of the sodium carboxymethyl cellulose used in Example 1 and 9 g of purified water were introduced into the trimix kneader used in Example 1 and then were mixed and kneaded under the same conditions as Example 1. A part (10 mg) of the dough was weighed into a 50-mL glass vial. After that, 20 mL of purified water was put into the glass vial, and then a mixture of the dough and water was served to same dispersion treatment as Example 1. The particle diameter distribution of turmeric nano-powder measured by the particle diameter distribution measurement instrument used in Example 1 was as follows: the average particle diameter ($D_{av}$)=379 nm, the value of $D_{10}$=155 nm, the value of $D_{50}$=298 nm, and the value of $D_{90}$=603 nm.

(2) A Process of Dispersion 270 g of purified water was added to 30 g of the dough. Then, a mixture of the dough and water was served to the dispersion treatment by the same conditions as Example 1.

(3) A Process of Drying

Next, the dispersion solution obtained in the foregoing process of dispersion was served into a freeze dryer (type of FDU-2100, EYELA). As a result, 27.5 g of dry powder was obtained. A part (10 mg) of the obtained dry powder was mixed with 20 mL of purified water. Then, a mixture of the dry powder and water was served to the dispersion treatment using the bath-type ultrasonic disperser used in Example 1 for 1 to 2 minutes. The particle diameter distribution of turmeric nano-powder measured by the foregoing particle diameter distribution measurement instrument after the dispersion treatment was as follows: the average particle diameter ($D_{av}$)=463 nm, the value of $D_{10}$=147 nm, the value of $D_{50}$=359 nm, and the value of $D_{90}$=802 nm.

Comparative Example 1

Preparation of a Turmeric-Containing Powder by Milling with Salt (1) Processes of Mixing and Milling 10 g of synthetic curcumin powder (manufactured by Wako Pure Chemical Industries, Ltd.), 80 g of milled salt (manufactured by Wako Pure Chemical Industries, Ltd.) and 17.2 g of glycerin (manufactured by Kanto Chemical Co., Inc.) were introduced into the trimix kneader used in Example 1 and then were mixed and kneaded under the same conditions as Example 1. The particle diameter distribution of the synthetic curcumin powder measured by using the particle diameter distribution measurement instrument used in Example 1 before the process of mixing was as follows: the average particle diameter ($D_{av}$)=17270 nm, the value of $D_{10}$=4422 nm, the value of $D_{50}$=15070 nm, and the value of $D_{90}$=33850 nm. 300 mg of the dough obtained after kneading was weighed into a 50-mL glass vial. After that, 5 mL of mixed solution of 0.1% SDS (sodium dodecylsulfate) and 0.1% hydrogenated soy bean lecithin was put into the glass vial. The content in the glass vial was served to the dispersion treatment by using the bath-type ultrasonic disperser used in Example 1 for 1 to 2 minutes. Dispersed content was added 45 mL of purified water and then was again served to the dispersion treatment by using the bath-type ultrasonic disperser for 1 to 2 minutes. The particle diameter distribution of synthetic curcumin nano-powder measured by the foregoing particle diameter distribution measurement instrument after the dispersion treatment was as follows: the average particle diameter ($D_{av}$)=96 nm, the value of $D_{10}$=37 nm, the value of $D_{50}$=78 nm, and the value of $D_{90}$=162 nm.

(2) A Process of Water-Washing 300 mg of the dough was weighed into a 50-mL falcon tube and then added 10 mL of purified water. After dispersed by a vortex, centrifugal separation was carried out by using a table-top centrifugal separator (number of rotation: 6000 rpm, for 10 minutes). Thereafter, the supernatant solution was discarded. Then, the centrifugal separation was carried out again after 10 mL of purified water was added to the residue. Such a set of operation was repeated until the electric conductivity of the final supernatant solution became 10 μs/cm or less, whereby producing a wet cake (this contained about 30 mg of curcumin). The Wet cake was added 5 mL of a mixed solution of 0.1% SDS (sodium dodecylsulfate) and 0.1% hydrogenated soy bean lecithin, and then was subjected to a dispersion treatment by using the foregoing bath-type ultrasonic disperser for 1 to 2 minutes. Then, the solution dispersed above was added 45 mL of purified water, and was again subjected to a dispersion treatment by using the foregoing bath-type ultrasonic disperser for 1 to 2 minutes. The particle diameter distribution of the synthetic curcumin nano-powder measured by the foregoing particle diameter distribution measurement instrument after the dispersion treatment was as follows: the average particle diameter ($D_{av}$)=255 nm, the value of $D_{av}$)=102 nm, the value of $D_{50}$=192 nm, and the value of $D_{90}$=431 nm.

(3) A Process of Drying

The wet cake obtained by the same procedure as the water-washing process was dried under vacuum (conditions: 30 degrees C. or lower, 1 hPa and 18 hours) to obtain 28 mg of dry powder. The dry powder obtained using above method was added 5 mL of a mixed solution of 0.1% SDS (sodium dodecylsulfate) and 0.1% hydrogenated soy bean lecithin and then was subjected to a dispersion treatment by using the foregoing bath-type ultrasonic disperser for 1 to 2 minutes. Then, the solution dispersed above was added 45 mL of purified water, and was again subjected to a dispersion treatment by using the foregoing bath-type ultrasonic disperser for 1 to 2 minutes. The particle diameter distribution of the synthetic curcumin powder measured by the foregoing particle diameterdistribution measurement instrument after the dispersion treatment was as follows: the average particle diameter $(D_{av})$=3048 nm, the value of $D_{10}$=133 nm, the value of $D_{50}$=507 nm, and the value of $D_{90}$=9376 nm.

Table 1 shows the particle diameter distributions of the products obtained in each process of Example 1, Example 2 and Comparative Example 1.

TABLE 1

| | Particle diameter distribution (nm) | | | | | | | | | | | |
|---|---|---|---|---|---|---|---|---|---|---|---|---|
| | After milling | | | | After water-washing | | | | After drying | | | |
| | Dav | D10 | D50 | D90 | Dav | D10 | D50 | D90 | Dav | D10 | D50 | D90 |
| Example 1 | 202 | 78 | 162 | 338 | — | — | — | — | 223 | 99 | 185 | 336 |
| Example 2 | 379 | 155 | 298 | 603 | — | — | — | — | 463 | 147 | 359 | 802 |
| Comparative Example 1 | 96 | 37 | 78 | 162 | 255 | 102 | 192 | 431 | 3048 | 133 | 507 | 9376 |

As shown in Table 1, without the process of drying, finer nano-powder was obtained by the conventional milling method used the salt, while with the process of drying, the powder obtained by milling method used the salt tended to agglomerate more easily. On the other hand, in the milling methods of Examples 1 and 2 used D-mannitol, even with the process of drying, nano-powder having the particle diameter distribution not significantly changed from the particle diameter distribution of the powder immediately after the milling could be obtained. This means that the particles in the powder become difficult to agglomerate after drying by milling with D-mannitol.

Example 3

Preparation of Powder Containing 10% by Weight of Rutin (1) Processes of Mixing and Milling 10 g of rutin powder (manufactured by Wako Pure Chemical Industries, Ltd.), 80 g of D-(−)-mannitol used in Example 1, 10 g of the sucrose fatty acid ester used in Example 1, 2.0 g of sodium carboxymethyl cellulose used in Example 1 and 10 g of purified water were introduced into a 500-mL trimix kneader (manufactured by Inoue MFG., Inc.), and then were mixed and kneaded under the same conditions as Example 1. The particle diameter distribution of the rutin powder measured by the particle diameter distribution measurement instrument used in Example 1 before the process of mixing was as follows: the average particle diameter $(D_{av})$=8949 nm, the value of $D_{10}$=1972 nm, the value of $D_{50}$=5007 nm, and the value of $D_{90}$=21450 nm. A part of the dough (30 mg) after the mixing and kneading was weighed into a 50-mL glass vial and then added 3 mL of 10% mannitol solution. Then, the solution obtained above was subjected to a dispersion treatment by using the bath-type ultrasonic disperser used in Example 1 for 0.5 to 1 minutes. The particle diameter distribution of rutin nano-powder measured by the foregoing particle diameter distribution measurement instrument after the dispersion treatment of the kneaded product was as follows: the average particle diameter $(D_{av})$=277 nm, the value of $D_{10}$=136 nm, the value of $D_{50}$=226 nm, and the value of $D_{90}$=410 nm.

(2) A Process of Drying

The dough (10 g) obtained in the foregoing process was dried in a vacuum dryer (type of VOS-300VD, EYELA) to obtain 9.27 g of dry powder. A part of the obtained dry powder (30 mg) was mixed with 3 mL of 10% mannitol solution and then was subjected to a dispersion treatment by using the foregoing bath-type ultrasonic disperser for 0.5 to 1 minutes. The particle diameter distribution of the rutin nano-powder measured by the foregoing particle diameter distribution measurement instrument after the dispersion treatment was as follows: the average particle diameter $(D_{av})$=321 nm, the value of $D_{10}$=140 nm, the value of $D_{50}$=265 nm, and the value of $D_{90}$=492 nm.

Example 4

Preparation of Kneaded Product Containing 45% by Weight of Fexofenadine Hydrochloride (1) Processes of Mixing and Milling 20 g of fexofenadine hydrochloride powder (manufactured by Sumitomo Chemical Co., Ltd.), 20 g of D-(−)-mannitol used in Example 1, 2 g of hydroxypropyl cellulose (trade name of SSL, manufactured by Nippon Soda Co., Ltd.) and 13.3 g of 10% polyvinyl alcohol (trade name of Poval 217C, manufactured by Kuraray Co., Ltd.) were introduced into the trimix kneader used in Example 1 and then were mixed and kneaded under the same conditions as Example 1. The particle diameter distribution of the fexofenadine hydrochloride powder measured by the particle diameter distribution measurement instrument used in Example 1 before the process of mixing was as follows: the average particle diameter $(D_{av})$=45660 nm, the value of $D_{10}$=3225 nm, the value of $D_{50}$=27320 nm, and the value of $D_{90}$=139600 nm. A part of the dough (15 mg) after the mixing and kneading was weighed into a 50-mL glass vial and then added 5 mL of a 0.4% aqueous sodium chloride solution. Then, the solution obtained above was subjected to a dispersion treatment by using the bath-type ultrasonic disperser used in Example 1 for 0.5 to 1 minutes. The particle diameter distribution of fexofenadine hydrochloride nano-powder measured by the foregoing particle diameter distribution measurement instrument after the dispersion treatment of the kneaded product was as follows: the average particle diameter $(D_{av})$=316 nm, the value of $D_{10}$=142 nm, the value of $D_{50}$=250 nm, and the value of $D_{90}$=489 nm.

(2) A Process of Drying

The dough (20 g) obtained in the foregoing process was dried in the vacuum dryer used in Example 3 to obtain 15.5 g of dry powder. A part of the obtained dry powder (15 mg) was mixed with 5 mL of a 0.4% aqueous sodium chloride solution and then was subjected to a dispersion treatment by using a probe-type ultrasonic disperser (probe-type 419 with Amp. of 25 for 1 minute, S4000 type, Astrason). The particle diameter distribution of the fexofenadine hydrochloride nano-powder measured by the foregoing particle diameter distribution measurement instrument after the dispersion treatment was as follows: the average particle diameter $(D_{av})$=230 nm, the value of $D_{10}$=129 nm, the value of $D_{50}$=198 nm, and the value of $D_{90}$=309 nm.

Example 5

Experiment 2

Preparation of Fluorometholone-Containing Ophthalmic Formulation (1) Processes of Mixing and Milling 8 g of fluorometholone powder (manufactured by Sicor Biotech UAB), 32 g of D-(−)-mannitol used in Example 1, 40 g of milled salt (trade name of Tomita Salt K-30, manufactured by Tomita Pharmaceutical Co., Ltd.) and 14 g of glycerin (manufactured by Wako Pure Chemical Industries, Ltd.) were introduced into the trimix kneader used in Example 1 and then were mixed and kneaded under the same conditions as Example 1. The particle diameter distribution of the fluorometholone powder measured by the particle diameter distribution measurement instrument used in Example 1 before the process of mixing was as follows: the average particle diameter $(D_{av})$=3148 nm, the value of $D_{10}$=1389 nm, the value of $D_{50}$=2636 nm, and the value of $D_{90}$=5709 nm. A part of the dough (60 mg) after the mixing and kneading was weighed into a 50-mL glass vial and then added 5 mL of a mixed solution of 0.1% SDS and 0.1% hydrogenated soy bean lecithin. Then, the solution obtained above was subjected to a dispersion treatment by using the foregoing bath-type ultrasonic disperser for 1 to 2 minutes. The particle diameter distribution of fluorometholone nano-powder measured by the foregoing particle diameter distribution measurement instrument after the dispersion treatment was as follows: the average particle diameter $(D_{av})$=136 nm, the value of $D_{10}$=68 nm, the value of $D_{50}$=114 nm, and the value of $D_{90}$=202 nm.

(2) A Process of Dispersion 4.5 g of the dough obtained in the foregoing process was added 36 g of 1.0% HCO60, 36 g of 1.0% HEC and 36 g of 0.01% benzarconium chloride and then was subjected to a dispersion treatment by using a probe-type ultrasonic disperser (probe-type 406HWS with Amp. of 30 for 4 minutes, 54000 type, Astrason). Then, 36 g of a mixture solution comprising 6% disodium phosphate dodecahydrate, 0.6% sodium dihydrogen phosphate dihydrate and 0.1% EDTA.2Na, and 36 g of 1.0% methyl cellulose was added thereinto and then purified water was further added thereinto in order to preapre 360 g of the mixture. Then, the solution obtained above was subjected to a dispersion treatment by using the probe-type ultrasonic disperser (probe-type 406HWS with Amp. of 30 for 1 minute, 54000 type, Astrason). Thus prepared formulation had the quality of passing through a 0.2 μm membrane filter almost thoroughly (passing rate of 90% or higher by HPLC analysis) and was with the particle diameter thereof coincident very well with that of the dough. Meanwhile, the osmotic pressure rate of the prepared formulation was about 1 (0.3 Osmol/kg $H_2O$), so the formulation could be used as an ophthalmic formulation as it was.

Example 6

Experiment 3

Preparation of Clarithromycin-Containing Drug (1) Processes of Mixing and Milling 10 g of clarithromycin powder (manufactured by Assia Chemical Industries Ltd.), 60 g of D-(−)-mannitol used in Example 1, 10 g of the milled salt used in Example 5, 3 g of polyvinyl pyrrolidone, 5.0 g of hydrogenated soy bean lecithin (manufactured by H. Holstein GmbH) and 20 g of glycerin were introduced into the trimix kneader used in Example 1, and then were mixed and kneaded under the same conditions as Example 1. The particle diameter distribution of the clarithromycin powder measured by the particle diameter distribution measurement instrument used in Example 1 before the process of mixing was as follows: the average particle diameter $(D_{av})$=10160 nm, the value of $D_{10}$=2277 nm, the value of $D_{50}$=6872 nm, and the value of $D_{90}$=22850 nm. A part of the dough (100 mg) after the mixing and kneading was weighed into a 50-mL glass vial and then added 3 mL of 0.1% HCO60. The solution obtained above was subjected to a dispersion treatment by using the foregoing bath-type ultrasonic disperser for 3 minutes. The particle diameter distribution of clarithromycin nano-powder measured by the foregoing particle diameter distribution measurement instrument after the dispersion treatment was as follows: the average particle diameter $(D_{av})$=145 nm, the value of $D_{10}$=81 nm, the value of $D_{50}$=125 nm, and the value of $D_{90}$=197 nm.

(2) A Process of Dispersion 1.3 g of the obtained dough was added 65 g of 0.1% HCO60 and 13 g of 2.0% hypromellose and then was subjected to a dispersion treatment by using the foregoing bath-type ultrasonic disperser for 10 minutes. Then, purified water was added thereinto in order to prepare 130 g of the mixture, which was then further subjected to a dispersion treatment by using the foregoing bath-type ultrasonic disperser for 1 minute. Thus prepared formulation had the quality of passing through a 0.2-μm membrane filter almost thoroughly (passing rate of 90% or higher by HPLC analysis) and was with the particle diameter thereof coincident very well with that of the dough. Meanwhile, the osmotic pressure rate of the prepared formulation was about 1 (0.3 Osmol/kg $H_2O$), so the formulation could be used as an ophthalmic formulation as it was.

As shown above, when the organic compound is milled by using a carbohydrate compound such as mannitol, an organic compound nano-powder or a suspension containing the powder can be produced in so simple process without the water-washing process, so that recovery loss of the powder can be avoided. In addition, because the water-washing process is not necessary, the particles of the organic compound are difficult to agglomerate. As a result, the diameter of the particles in the dough obtained immediately after milling may be kept.

Table 2 shows granular carbohydrate compounds used in following experiments. The term "Dav" means an average particle diameter $(D_{av})$. In the table, the term "D10" means the particle diameter ($D_{10}$ value) of the particle at the position of 10% when counted from the smallest size zero (minimum) to 100% (maximum) of the particle diameter in a particle diameter distribution. The term "D50" means a certain particle diameter ($D_{50}$ value) when amount of a larger side becomes equal to amount of a smaller side of the particle diameters divided into two a powder from the certain particle diameter. The term "D90" means the particle diameter ($D_{90}$ value) of the particle at the position of 90% when counted from the smallest size zero (minimum) to 100% (maximum) of the particle diameter in the particle diameter distribution. The same definitions shall apply to following tables.

TABLE 2

| Carbohydrate compound | Particle Size (μm) | | | | Melting point (Degrees C.) | Supplyer |
|---|---|---|---|---|---|---|
| | Dav | D10 | D50 | D90 | | |
| Mannitol | 79 | 24 | 66 | 144 | 166-168 | Kanto Chemical Co., Inc. (High grade) |
| Maltitol | 33 | 7 | 30 | 64 | 145 | Mitsubishi Shoji Foodtech Co., Ltd. |
| Sorbitol | 159 | 75 | 154 | 249 | 95 | Kanto Chemical Co., Inc. (Cica first grade) |
| Erythritol | 147 | 63 | 138 | 237 | 121 | B Food Science Co., Ltd. |
| Xylitol | 631 | 383 | 615 | 912 | 92-96 | Wako Pure Chemical Industries, Ltd. (High grade) |
| Inositol | 280 | 116 | 247 | 496 | 225-227 | Tsuno Rice Fine Chemicals Co., Ltd. |
| Glucose | 238 | 135 | 231 | 355 | 146-150 | Wako Pure Chemical Industries, Ltd. (High grade) |
| Fructose | 339 | 158 | 311 | 566 | 104 | Wako Pure Chemical Industries, Ltd. (High grade) |
| Lactose monohydrate | 45 | 3 | 20 | 123 | 202 | Kanto Chemical Co., Inc. (High grade) |
| Trehalose | 25 | 7 | 20 | 50 | 203 | Hayashibara Co., Ltd. |
| Cellobiose | 41 | 7 | 38 | 76 | 225 (Decomposition) | Nippon Paper Industries Co., Ltd. Chemical division |
| Dextrin | 38 | 16 | 38 | 63 | — | Wako Pure Chemical Industries, Ltd. |

Experiment 4

Milling with D-Mannitol

Example 7

Preparation of a Curcumin Nano-Powder 100 mg of turmeric powder (70% or more purity of curcumin, or 90% or more purity of curcuminoid, manufactured by Bio Actives Japan Corp.), 325 mg of D-(−)-mannitol used in Example 1, 50 mg of sucrose fatty acid ester (trade name of DK Ester SS, manufactured by Dai-Ichi Kogyo Seiyaku Co., Ltd.), 9 mg of sodium carboxymethyl cellulose (trade name of Cellogen F-3H, manufactured by Dai-Ichi Kogyo Seiyaku Co., Ltd.) and 110 mg of purified water were served on a glass disk of a Hoover muller (manufactured by Imoto Machinery Co., Ltd.) and then kneaded by repeating five times to rotate the disk in 20 turns per time. Above-served contents formed a kind of dough during kneading and whereby the turmeric powder was finely milled. Hereinafter, the term "turmeric powder" will be also called as another term "curcumin" for the reason that curcumin is a major ingredient in the turmeric powder. 10 mg of the dough obtained after milling was weighed into a 50-mL glass vial and then added 5 mL of a mixed solution of 0.1% sodium dodecylsulfate (manufactured by Wako Pure Chemical Industries, Ltd.) and 0.01% hydrogenated soy bean lecithin (trade name of Phospholipon 90H, manufactured by Lipoid GmbH). Then, the solution obtained above was subjected to a dispersion treatment by using a bath-type ultrasonic disperser (type of US100 III, manufactured by AS ONE Corp., the same shall apply hereinafter) for 1 to 2 minutes. The particle diameter distribution of curcumin nano-powder measured by the same particle diameter distribution measurement instrument as used in Example 1 was as follows: $D_{av}$=384 nm, the value of $D_{10}$=154 nm, the value of $D_{50}$=280 nm, and the value of $D_{90}$=569 nm.

Example 8

Preparation of a Mefenamic Acid Nano-Powder

A mefenamic acid powder was milled and then subjected to a dispersion treatment under the same conditions as Example 7 except changing from 100 mg of turmeric powder to 100 mg of mefenamic acid powder (manufactured by Tokyo Chemical Industry Co., Ltd.). As a result, the particle diameter distribution of mefenamic acid nano-powder obtained after above procedures was as follows: $D_{av}$=247 nm, the value of $D_{10}$=99 nm, the value of $D_{50}$=198 nm, and the value of $D_{90}$=403 nm.

Example 9

Preparation of an Acetaminophen Nano-Powder

An acetaminophen powder was milled under the same conditions as Example 7 except both changing from 100 mg of turmeric powder to 100 mg of acetaminophen powder (manufactured by Tokyo Chemical Industry Co., Ltd.) and changing from sucrose fatty acid ester to decaglyceryl monostearate (trade name of Decaglyn 1-SV, manufactured by Nikko Chemicals Co., Ltd.). Then, 100 mg of the dough obtained after milling was weighed and then subjected to a dispersion treatment under the same conditions as Example 7 except adding only 5 mL of 0.1% sodium dodecylsulfate (same as used in Example 7 and also used in following experiments) but no 0.01% hydrogenated soy bean lecithin (same as used in Example 7 and also used in following experiments). As a result, the particle diameter distribution of acetaminophen nano-powder obtained after above procedures was as follows: $D_{av}$=443 nm, the value of $D_{10}$=92 nm, the value of $D_{50}$=286 nm, and the value of $D_{90}$=886 nm.

Example 10

Preparation of an Ibuprofen Nano-Powder

An ibuprofen powder was milled under the same conditions as Example 7 except both changing from 100 mg of turmeric powder to 100 mg of ibuprofen powder (manufactured by Tokyo Chemical Industry Co., Ltd.) and changing from sucrose fatty acid ester to hydrogenated soy bean lecithin. Then, the dough obtained after milling was subjected to a dispersion treatment under the same conditions as Example 7 except adding 10 mL of a mixed solution of 0.1% sodium dodecylsulfate and 0.01% hydrogenated soy bean lecithin. As a result, the particle diameter distribution of ibuprofen nano-powder obtained after above procedures was as follows: $D_{av}$=286 nm, the value of $D_{10}$=71 nm, the value of $D_{50}$=122 nm, and the value of $D_{90}$=257 nm.

Example 11

Preparation of an Amphotericin B Nano-Powder

An amphotericin B powder was milled under the same conditions as Example 7 except both changing from 100 mg of turmeric powder to 100 mg of amphotericin B powder (manufactured by Wako Pure Chemical Industries, Ltd.) and changing from sucrose fatty acid ester to hydrogenated soy bean lecithin. Then, the dough obtained after milling was subjected to a dispersion treatment under the same conditions as Example 7 except adding only 5 mL of 0.1% sodium dodecylsulfate but no 0.01% hydrogenated soy bean lecithin. As a result, the particle diameter distribution of amphotericin B nano-powder obtained after above procedures was as follows: $D_{av}$=242 nm, the value of $D_{10}$=87 nm, the value of $D_{50}$=195 nm, and the value of $D_{90}$=397 nm.

Example 12

Preparation of a Diclofenac Sodium Nano-Powder

A diclofenac sodium powder was milled under the same conditions as Example 7 except both changing from 100 mg of turmeric powder to 100 mg of diclofenac sodium powder (manufactured by Tokyo Chemical Industry Co., Ltd.) and changing from sucrose fatty acid ester to decaglyceryl monostearate (same as used in Example 9 and also used in following experiments). Then, 100 mg of the dough obtained after milling was weighed and then subjected to a dispersion treatment under the same conditions as Example 7 except adding only 5 mL of 0.1% sodium dodecylsulfate but no 0.01% hydrogenated soy bean lecithin. As a result, the particle diameter distribution of diclofenac sodium nano-powder obtained after above procedures was as follows: $D_{av}$=303 nm, the value of $D_{10}$=99 nm, the value of $D_{50}$=228 nm, and the value of $D_{90}$=536 nm.

Example 13

Preparation of an Indomethacin Nano-Powder

An indomethacin powder was milled under the same conditions as Example 7 except changing from 100 mg of turmeric powder to 100 mg of indomethacin powder (manufactured by Wako Pure Chemical Industries, Ltd.). Then, the dough obtained after milling was subjected to a dispersion treatment under the same conditions as Example 7 except adding only 10 mL of 0.1% sodium dodecylsulfate but no 0.01% hydrogenated soy bean lecithin. As a result, the particle diameter distribution of indomethacin nano-powder obtained after above procedures was as follows: $D_{av}$=353 nm, the value of $D_{10}$=155 nm, the value of $D_{50}$=289 nm, and the value of $D_{90}$=539 nm.

Example 14

Preparation of a Felbinac Nano-Powder

A felbinac powder was milled under the same conditions as Example 7 except changing from 100 mg of turmeric powder to 100 mg of felbinac powder (manufactured by Wako Pure Chemical Industries, Ltd.). Then, the dough obtained after milling was subjected to a dispersion treatment under the same conditions as Example 7 except adding 10 mL of 0.1% sodium dodecylsulfate but no 0.01% hydrogenated soy bean lecithin. As a result, the particle diameter distribution of felbinac nano-powder obtained after above procedures was as follows: $D_{av}$=335 nm, the value of $D_{10}$=170 nm, the value of $D_{50}$=279 nm, and the value of $D_{90}$=481 nm.

Example 15

Preparation of a Pranlukast Hydrate Nano-Powder

A pranlukast hydrate powder was milled under the same conditions as Example 7 except changing from 100 mg of turmeric powder to 100 mg of pranlukast hydrate powder (manufactured by Hallochem Pharma. Co., Ltd., China). Then, the dough obtained after milling was subjected to a dispersion treatment under the same conditions as Example 7 except adding only 10 mL of 0.1% sodium dodecylsulfate but no 0.01% hydrogenated soy bean lecithin. As a result, the particle diameter distribution of pranlukast hydrate nano-powder obtained after above procedures was as follows: $D_{av}$=152 nm, the value of $D_{10}$=85 nm, the value of $D_{50}$=132 nm, and the value of $D_{90}$=208 nm.

Example 16

Preparation of a Dexamethasone Nano-Powder

A dexamethasone powder was milled under the same conditions as Example 7 except changing from 100 mg of turmeric powder to 100 mg of dexamethasone powder (manufactured by Wako Pure Chemical Industries, Ltd.). Then, 20 mg of the dough obtained after milling was weighed and then subjected to a dispersion treatment under the same conditions as Example 7 except adding only 5 mL of 0.1% Polyoxyethylene Hydrogenated Castor Oil 60 (trade name of NIKKOL HCO-60, manufactured by Nikko Chemicals Co., Ltd.). As a result, the particle diameter distribution of dexamethasone nano-powder obtained after above procedures was as follows: $D_{av}$=179 nm, the value of $D_{10}$=102 nm, the value of $D_{50}$=155 nm, and the value of $D_{90}$=240 nm.

Comparative Example 2

Milling of a Curcumin Powder without Using D-Mannitol

The turmeric powder used in Example 7 was milled under the same conditions as Example 7 except adding no D-(−)- mannitol. Then, 2 mg of the dough obtained after milling was weighed into a 50-mL glass vial and then subjected to a dispersion treatment under the same conditions as Example 7. As a result, the particle diameter distribution of curcumin powder obtained after above procedures was as follows: $D_{av}$=716 nm, the value of $D_{10}$=131 nm, the value of $D_{50}$=216 nm, and the value of $D_{90}$=2983 nm. Thus, the $D_{av}$ and the $D_{90}$ of the particle diameter distribution were more than 500 nm and 1500 nm, respectively.

Comparative Example 3

Milling of a Mefenamic Acid Powder without Using D-Mannitol

The mefenamic acid powder used in Example 8 was milled under the same conditions as Example 8 except adding no D-(−)-mannitol. Then, 2 mg of the dough obtained after milling was weighed into a 50-mL glass vial and then subjected to a dispersion treatment under the same conditions as Example 8. As a result, the particle diameter distribution of mefenamic acid powder obtained after above procedures was as follows: $D_{av}$=926 nm, the value of $D_{10}$=155 nm, the value of $D_{50}$=276 nm, and the value of $D_{90}$=3673 nm. Thus, the $D_{av}$ and the $D_{90}$ of the particle diameter distribution were more than 500 nm and 1500 nm, respectively.

Comparative Example 4

Milling of an Acetaminophen Powder without Using D-Mannitol

The acetaminophen powder used in Example 9 was milled under the same conditions as Example 9 except adding no D-(−)-mannitol. Then, 20 mg of the dough obtained after milling was weighed into a 50-mL glass vial and then subjected to a dispersion treatment under the same conditions as Example 9. As a result, the particle diameter distribution of acetaminophen powder obtained after above procedures was as follows: $D_{av}$=1124 nm, the value of $D_{10}$=134 nm, the value of $D_{50}$=400 nm, and the value of $D_{90}$=2899 nm. Thus, the $D_{av}$ and the $D_{90}$ of the particle diameter distribution were more than 500 nm and 1500 nm, respectively.

Comparative Example 5

Milling of an Ibuprofen Powder without Using D-Mannitol

The ibuprofen powder used in Example 10 was milled under the same conditions as Example 10 except adding no D-(−)-mannitol. Then, 2 mg of the dough obtained after milling was weighed into a 50-mL glass vial and then subjected to a dispersion treatment under the same conditions as Example 10. As a result, the particle diameter distribution of ibuprofen powder obtained after above procedures was as follows: $D_{av}$=2873 nm, the value of $D_{10}$=403 nm, the value of $D_{50}$=619 nm, and the value of $D_{90}$=10421 nm. Thus, the $D_{av}$ and the $D_{90}$ of the particle diameter distribution were more than 500 nm and 1500 nm, respectively.

Comparative Example 6

Milling of an Amphotericin B Powder without Using D-Mannitol

The amphotericin B powder used in Example 11 was milled under the same conditions as Example 11 except adding no D-(−)-mannitol. Then, 2 mg of the dough obtained after milling was weighed into a 50-mL glass vial and then subjected to a dispersion treatment under the same conditions as Example 11. As a result, the particle diameter distribution of amphotericin B powder obtained after above procedures was as follows: $D_{av}$=750 nm, the value of $D_{10}$=159 nm, the value of $D_{50}$=314 nm, and the value of $D_{90}$=841 nm Thus, the $D_{av}$ of the particle diameter distribution was more than 500 nm.

Comparative Example 7

Milling of a Diclofenac Sodium Powder without Using D-Mannitol

The diclofenac sodium powder used in Example 12 was milled under the same conditions as Example 12 except adding no D-(−)-mannitol. Then, 20 mg of the dough obtained after milling was weighed into a 50-mL glass vial and then subjected to a dispersion treatment under the same conditions as Example 12. As a result, the particle diameter distribution of diclofenac sodium powder obtained after above procedures was as follows: $D_{av}$=589 nm, the value of $D_{10}$=78 nm, the value of $D_{50}$=196 nm, and the value of $D_{90}$=2364 nm. Thus, the $D_{av}$ and the $D_{90}$ of the particle diameter distribution were more than 500 nm and 1500 nm, respectively.

Comparative Example 8

Milling of an Indomethacin Powder without Using D-Mannitol

The indomethacin powder used in Example 13, 30 mg of polyvinylpyrrolidone (trade name of K25, manufactured by Wako Pure Chemical Industries, Ltd.), 50 mg of hydrogenated soy bean lecithin and 50 mg of glycerin (manufactured by Junsei Chemical Co., Ltd.) were served on a glass disk of a Hoover muller (same as used in Example 7 and also used in following experiments) without adding D-(−)-mannitol and then kneaded by repeating five times to rotate the disk in 20 turns per time. Above-served contents formed a kind of dough during kneading and whereby the indomethacin powder was milled 2 mg of the dough obtained after milling was weighed into a 50-mL glass vial and then subjected to a dispersion treatment under the same conditions as Example 13. As a result, the particle diameter distribution of indomethacin powder obtained after above procedures was as follows: $D_{av}$=1346 nm, the value of $D_{10}$=145 nm, the value of $D_{50}$=219 nm, and the value of $D_{90}$=4154 nm. Thus, the $D_{av}$ and the $D_{90}$ of the particle diameter distribution were more than 500 nm and 1500 nm, respectively.

Comparative Example 9

Milling of a Felbinac Powder without Using D-Mannitol

The felbinac powder used in Example 14, 30 mg of polyvinylpyrrolidone (same as used in Comparative Example 8 and also used in following experiments), 50 mg of hydrogenated soy bean lecithin and 50 mg of glycerin (same as used in Comparative Example 8 and also used in following experiments) were served on a glass disk of the foregoing Hoover muller without adding D-(−)-mannitol and then kneaded by repeating five times to rotate the disk in 20 turns per time. Above-served contents formed a kind of dough during kneading and whereby the felbinac powder was milled 2 mg of the dough obtained after milling was weighed into a 50-mL glass vial and then subjected to a dispersion treatment under the same conditions as Example 14. As a result, the particle diameter distribution of felbinac powder obtained after above procedures was as follows: $D_{av}$=1457 nm, the value of $D_{10}$=154 nm, the value of $D_{50}$=309 nm, and the value of $D_{90}$=5452 nm. Thus, the $D_{av}$ and the $D_{90}$ of the particle diameter distribution were more than 500 nm and 1500 nm, respectively.

Comparative Example 10

Milling of a Pranlukast Hydrate Powder without Using D-Mannitol

The pranlukast hydrate powder used in Example 15 (also used in following experiments), 30 mg of polyvinylpyrrolidone, 50 mg of hydrogenated soy bean lecithin and 75 mg of glycerin were served on a glass disk of the foregoing Hoover muller without adding D-(−)-mannitol and then kneaded by repeating five times to rotate the disk in 20 turns per time. Above-served contents formed a kind of dough during kneading and whereby the pranlukast hydrate powder was milled 2 mg of the dough obtained after milling was weighed into a 50-mL glass vial and then subjected to a dispersion treatment under the same conditions as Example 15. As a result, the particle diameter distribution of pranlukast hydrate powder obtained after above procedures was as follows: $D_{av}$=1102 nm, the value of $D_{10}$=129 nm, the value of $D_{50}$=408 nm, and the value of $D_{90}$=4226 nm. Thus, the $D_{av}$ and the $D_{90}$ of the particle diameter distribution were more than 500 nm and 1500 nm, respectively.

Comparative Example 11

Milling of a Dexamethasone Powder without Using D-Mannitol

The dexamethasone powder used in Example 16, 30 mg of polyvinylpyrrolidone, 50 mg of hydrogenated soy bean lecithin and 50 mg of glycerin were served on a glass disk of the foregoing Hoover muller without adding D-(−)-mannitol and then kneaded by repeating five times to rotate the disk in 20 turns per time. Above-served contents formed a kind of dough during kneading and whereby the dexamethasone powder was milled 4 mg of the dough obtained after milling was weighed into a 50-mL glass vial and then subjected to a dispersion treatment under the same conditions as Example 16. As a result, the particle diameter distribution of dexamethasone powder obtained after above procedures was as follows: $D_{av}$=3704 nm, the value of $D_{10}$=138 nm, the value of $D_{50}$=852 nm, and the value of $D_{90}$=12321 nm. Thus, the $D_{av}$ and the $D_{90}$ of the particle diameter distribution were more than 500 nm and 1500 nm, respectively.

Table 3 shows the particle diameter distributions of various organic compound powders prepared in Examples 7 to 16 and Comparative Examples 2 to 11 as compared with the particle diameter distributions of the powders before milling. The term "Cur" in the table means curcumin. The term "Mef" in the table means mefenamic acid. The term "Ace" in the table means acetaminophen. The term "Ibu" in the table means ibuprofen. The term "Amp" in the table means amphotericin B. The term "Dic" in the table means diclofenac sodium. The term "Ind" in the table means indomethacin. The term "Fel" in the table means felbinac. The term "Pra" in the table means pranlukast hydrate. The term "Dex" in the table means dexamethasone.

TABLE 3

| | Organic compound | Paticle diameter distribution (nm) | | | | | | | |
| --- | --- | --- | --- | --- | --- | --- | --- | --- | --- |
| | | Before milling | | | | After milling | | | |
| | | Dav | D10 | D50 | D90 | Dav | D10 | D50 | D90 |
| Example 7 | Cur | 16640 | 930 | 12150 | 35870 | 384 | 154 | 280 | 569 |
| Example 8 | Mef | 16130 | 770 | 13290 | 35550 | 247 | 99 | 198 | 403 |
| Example 9 | Ace | 109940 | 41240 | 103460 | 188510 | 443 | 92 | 286 | 886 |
| Example 10 | Ibu | 79030 | 23100 | 69440 | 149660 | 286 | 71 | 122 | 257 |
| Example 11 | Amp | 19660 | 510 | 12520 | 51740 | 242 | 87 | 195 | 397 |
| Example 12 | Dic | 77780 | 23400 | 68380 | 152090 | 303 | 99 | 228 | 536 |
| Example 13 | Ind | 12400 | 630 | 8670 | 30820 | 353 | 155 | 289 | 539 |
| Example 14 | Fel | 190720 | 46270 | 166710 | 356860 | 335 | 170 | 279 | 481 |
| Example 15 | Pra | 9500 | 1050 | 6150 | 23660 | 152 | 85 | 132 | 208 |
| Example 16 | Dex | 2690 | 280 | 2580 | 5360 | 179 | 102 | 155 | 240 |
| Comparative Example 2 | Cur | 16640 | 930 | 12150 | 35870 | 716 | 131 | 216 | 2983 |
| Comparative Example 3 | Mef | 16130 | 770 | 13290 | 35550 | 926 | 155 | 276 | 3673 |
| Comparative Example 4 | Ace | 109940 | 41240 | 103460 | 188510 | 1124 | 134 | 400 | 2899 |
| Comparative Example 5 | Ibu | 79030 | 23100 | 69440 | 149660 | 2873 | 403 | 619 | 10421 |
| Comparative Example 6 | Amp | 19660 | 510 | 12520 | 51740 | 750 | 159 | 314 | 841 |
| Comparative Example 7 | Dic | 77780 | 23400 | 68380 | 152090 | 589 | 78 | 196 | 2364 |
| Comparative Example 8 | Ind | 12400 | 630 | 8670 | 30820 | 1346 | 145 | 219 | 4154 |
| Comparative Example 9 | Fel | 190720 | 46270 | 166710 | 356860 | 1457 | 154 | 309 | 5452 |
| Comparative Example 10 | Pra | 9500 | 1050 | 6150 | 23660 | 1102 | 129 | 408 | 4226 |
| Comparative Example 11 | Dex | 2690 | 280 | 2580 | 5360 | 3704 | 138 | 852 | 12321 |

As shown in Table 3, organic compound nano-powder consisting of the particles with so small particle diameter was prepared when organic compound powder was milled with using D-mannitol as one of carbohydrate compounds. On the other hand, organic compound nano-powder consisting of the particles with $D_{av}$ of 500 nm or less and $D_{90}$ of 1500 nm or less were unable to prepare when the organic compound powder was milled without using D-mannitol. According to above results, it is considered that the carbohydrate compound contributes to increase the efficiency of milling the organic compound.

Experiment 5

Milling with Xylitol

Example 17

Preparation of a Curcumin Nano-Powder 100 mg of turmeric powder (same as used in Example 7 and also used in following experiments), 325 mg of xylitol, 50 mg of sucrose fatty acid ester (same as used in Example 7 and also used in following experiments), 9 mg of sodium carboxymethyl cellulose (same as used in Example 7 and also used in following experiments) and 110 mg of purified water were served on a glass disk of the foregoing Hoover muller and then kneaded by repeating five times to rotate the disk in 20 turns per time. Above-served contents formed a kind of dough during kneading and whereby the turmeric powder was finely milled 10 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using a bath-type ultrasonic disperser (same as used in Example 7 and also used in following experiments) for 1 to 2 minutes. As a result, the particle diameter distribution of curcumin nano-powder obtained after above procedures was as follows: $D_{av}$=283 nm, the value of $D_{10}$=138 nm, the value of $D_{50}$=234 nm, and the value of $D_{90}$=418 nm.

Example 18

Preparation of a Mefenamic Acid Nano-Powder

A mefenamic acid powder was milled and then subjected to a dispersion treatment under the same conditions as Example 17 except changing from 100 mg of turmeric powder to 100 mg of mefenamic acid powder (same as used in Example 8 and also used in following experiments). As a result, the particle diameter distribution of mefenamic acid nano-powder obtained after above procedures was as follows: $D_{av}$=241 nm, the value of $D_{10}$=98 nm, the value of $D_{50}$=191 nm, and the value of $D_{90}$=398 nm.

Example 19

Preparation of an Ibuprofen Nano-Powder

An ibuprofen powder was milled under the same conditions as Example 17 except changing from 100 mg of turmeric powder to 100 mg of ibuprofen powder (same as used in Example 10 and also used in following experiments). Then, the dough obtained after milling was subjected to a dispersion treatment under the same conditions as Example 17 except adding 10 mL of a mixed solution of 0.1% sodium dodecylsulfate and 0.01% hydrogenated soy bean lecithin. As a result, the particle diameter distribution of ibuprofen nano-powder obtained after above procedures was as follows: $D_{av}$=321 nm, the value of $D_{10}$=150 nm, the value of $D_{50}$=265 nm, and the value of $D_{90}$=477 nm.

Example 20

Preparation of an Amphotericin B Nano-Powder

An amphotericin B powder was milled under the same conditions as Example 17 except both changing from 100 mg of turmeric powder to 100 mg of amphotericin B powder (same as used in Example 11 and also used in following experiments) and changing from sucrose fatty acid ester to hydrogenated soy bean lecithin. Then, the dough obtained after milling was subjected to a dispersion treatment under the same conditions as Example 17 except adding only 5 mL of 0.1% sodium dodecylsulfate but no 0.01% hydrogenated soy bean lecithin. As a result, the particle diameter distribution of amphotericin B nano-powder obtained after above procedures was as follows: $D_{av}$=343 nm, the value of $D_{10}$=107 nm, the value of $D_{50}$=170 nm, and the value of $D_{90}$=326 nm.

Example 21

Preparation of a Diclofenac Sodium Nano-Powder

A diclofenac sodium powder was milled under the same conditions as Example 17 except both changing from 100 mg of turmeric powder to 100 mg of diclofenac sodium powder (same as used in Example 12 and also used in following experiments) and changing from sucrose fatty acid ester to decaglyceryl monostearate (same as used in Example 9 and also used in following experiments). Then, 100 mg of the dough obtained after milling was weighed and then subjected to a dispersion treatment under the same conditions as Example 17 except adding only 5 mL of 0.1% sodium dodecylsulfate but no 0.01% hydrogenated soy bean lecithin. As a result, the particle diameter distribution of diclofenac sodium nano-powder obtained after above procedures was as follows: $D_{av}$=200 nm, the value of $D_{10}$=58 nm, the value of $D_{50}$=178 nm, and the value of $D_{90}$=300 nm.

Table 4 shows the particle diameter distributions of various organic compound powders prepared in Examples 17 to 21 as compared with the particle diameter distributions of the powders before milling.

TABLE 4

|  | Organic compound | Particle diameter distribution (nm) | | | | | | | |
|---|---|---|---|---|---|---|---|---|---|
|  |  | Before milling | | | | After milling | | | |
|  |  | Dav | D10 | D50 | D90 | Dav | D10 | D50 | D90 |
| Example 17 | Cur | 16640 | 930 | 12150 | 35870 | 283 | 138 | 234 | 418 |
| Example 18 | Mef | 16130 | 770 | 13290 | 35550 | 241 | 98 | 191 | 398 |
| Example 19 | Ibu | 79030 | 23100 | 69440 | 149660 | 321 | 150 | 265 | 477 |
| Example 20 | Amp | 19660 | 510 | 12520 | 51740 | 343 | 107 | 170 | 326 |
| Example 21 | Dic | 77780 | 23400 | 68380 | 152090 | 200 | 58 | 178 | 300 |

As shown in Table 4, organic compound nano-powder consisting of the particles with so small particle diameter was prepared when organic compound powder was milled with using xylitol as one of carbohydrate compounds.

Experiment 6

Milling with Glucose

Example 22

Preparation of a Curcumin Nano-Powder 100 mg of turmeric powder, 325 mg of glucose, 50 mg of sucrose fatty acid ester, 9 mg of sodium carboxymethyl cellulose and 110 mg of purified water were served on a glass disk of the foregoing Hoover muller and then kneaded by repeating five times to rotate the disk in 20 turns per time. Above-served contents formed a kind of dough during kneading and whereby the turmeric powder was finely milled 10 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of curcumin nano-powder obtained after above procedures was as follows: $D_{av}$=345 nm, the value of $D_{10}$=96 nm, the value of $D_{50}$=242 nm, and the value of $D_{90}$=648 nm.

Example 23

Preparation of a Mefenamic Acid Nano-Powder

A mefenamic acid powder was milled and then subjected to a dispersion treatment under the same conditions as Example 22 except changing from 100 mg of turmeric powder to 100 mg of mefenamic acid powder. As a result, the particle diameter distribution of mefenamic acid nano-powder obtained after above procedures was as follows: $D_{av}$=224 nm, the value of $D_{10}$=85 nm, the value of $D_{50}$=193 nm, and the value of $D_{90}$=339 nm.

Example 24

Preparation of an Ibuprofen Nano-Powder

An ibuprofen powder was milled under the same conditions as Example 22 except both changing from 100 mg of turmeric powder to 100 mg of ibuprofen powder and changing from sucrose fatty acid ester to hydrogenated soy bean lecithin. Then, the dough obtained after milling was subjected to a dispersion treatment under the same conditions as Example 22 except adding 10 mL of a mixed solution of 0.1% sodium dodecylsulfate and 0.01% hydrogenated soy bean lecithin. As a result, the particle diameter distribution of ibuprofen nano-powder obtained after above procedures was as follows: $D_{av}$=327 nm, the value of $D_{10}$=156 nm, the value of $D_{50}$=266 nm, and the value of $D_{90}$=489 nm.

Example 25

Preparation of a Diclofenac Sodium Nano-Powder

A diclofenac sodium powder was milled under the same conditions as Example 22 except both changing from 100 mg of turmeric powder to 100 mg of diclofenac sodium powder and changing from sucrose fatty acid ester to decaglyceryl monostearate. Then, 100 mg of the dough obtained after milling was weighed and then subjected to a dispersion treatment under the same conditions as Example 22 except adding only 5 mL of 0.1% sodium dodecylsulfate but no 0.01% hydrogenated soy bean lecithin. As a result, the particle diameter distribution of diclofenac sodium nano-powder obtained after above procedures was as follows: $D_{av}$=244 nm, the value of $D_{10}$=78 nm, the value of $D_{50}$=130 nm, and the value of $D_{90}$=266 nm.

Table 5 shows the particle diameter distributions of various organic compound powders prepared in Examples 22 to 25 as compared with the particle diameter distributions of the powders before milling.

TABLE 5

|  | Organic compound | Particle diameter distibution (nm) | | | | | | | |
|---|---|---|---|---|---|---|---|---|---|
|  |  | Before milling | | | | After milling | | | |
|  |  | Dav | D10 | D50 | D90 | Dav | D10 | D50 | D90 |
| Example 22 | Cur | 16640 | 930 | 12150 | 35870 | 345 | 96 | 242 | 648 |
| Example 23 | Mef | 16130 | 770 | 13290 | 35550 | 224 | 85 | 193 | 339 |
| Example 24 | Ibu | 79030 | 23100 | 69440 | 149660 | 327 | 156 | 266 | 489 |
| Example 25 | Dic | 77780 | 23400 | 68380 | 152090 | 244 | 78 | 130 | 266 |

As shown in Table 5, organic compound nano-powder consisting of the particles with so small particle diameter was prepared when organic compound powder was milled with using glucose as one of carbohydrate compounds.

Experiment 7

Milling with Fructose

Example 26

Preparation of a Curcumin Nano-Powder 100 mg of turmeric powder, 325 mg of fructose, 50 mg of sucrose fatty acid ester, 9 mg of sodium carboxymethyl cellulose and 110 mg of purified water were served on a glass disk of the foregoing Hoover muller and then kneaded by repeating five times to rotate the disk in 20 turns per time. Above-served contents formed a kind of dough during kneading and whereby the turmeric powder was finely milled 10 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of curcumin nano-powder obtained after above procedures was as follows: $D_{av}$=181 nm, the value of $D_{10}$=82 nm, the value of $D_{50}$=144 nm, and the value of $D_{90}$=286 nm.

Example 27

Preparation of a Mefenamic Acid Nano-Powder

A mefenamic acid powder was milled and then subjected to a dispersion treatment under the same conditions as Example 26 except changing from 100 mg of turmeric powder to 100 mg of mefenamic acid powder. As a result, the particle diameter distribution of mefenamic acid nano-powder obtained after above procedures was as follows: $D_{av}$=205 nm, the value of $D_{10}$=84 nm, the value of $D_{50}$=165 nm, and the value of $D_{90}$=328 nm.

Example 28

Preparation of an Acetaminophen Nano-Powder

The acetaminophen powder was milled under the same conditions as Example 26 except both changing from 100 mg of turmeric powder to 100 mg of acetaminophen powder (same as used in Example 9 and also used in following experiments) and changing from sucrose fatty acid ester to decaglyceryl monostearate. Then, 100 mg of the dough obtained after milling was weighed and then subjected to a dispersion treatment under the same conditions as Example 26 except adding only 5 mL of 0.1% sodium dodecylsulfate but no 0.01% hydrogenated soy bean lecithin. As a result, the particle diameter distribution of acetaminophen nano-powder obtained after above procedures was as follows: $D_{av}$=186 nm, the value of $D_{10}$=82 nm, the value of $D_{50}$=148 nm, and the value of $D_{90}$=296 nm.

Example 29

Preparation of an Ibuprofen Nano-Powder

An ibuprofen powder was milled under the same conditions as Example 26 except changing from 100 mg of turmeric powder to 100 mg of ibuprofen powder. Then, the dough obtained after milling was subjected to a dispersion treatment under the same conditions as Example 26 except adding 10 mL of a mixed solution of 0.1% sodium dodecylsulfate and 0.01% hydrogenated soy bean lecithin. As a result, the particle diameter distribution of ibuprofen nano-powder obtained after above procedures was as follows: $D_{av}$=434 nm, the value of $D_{10}$=176 nm, the value of $D_{50}$=335 nm, and the value of $D_{90}$=711 nm.

Example 30

Preparation of an Amphotericin B Nano-Powder

An amphotericin B powder was milled under the same conditions as Example 26 except both changing from 100 mg of turmeric powder to 100 mg of amphotericin B powder and changing from sucrose fatty acid ester to hydrogenated soy bean lecithin. Then, the dough obtained after milling was subjected to a dispersion treatment under the same conditions as Example 26 except adding only 5 mL of 0.1% sodium dodecylsulfate but no 0.01% hydrogenated soy bean lecithin. As a result, the particle diameter distribution of amphotericin B nano-powder obtained after above procedures was as follows: $D_{av}$=376 nm, the value of $D_{10}$=132 nm, the value of $D_{50}$=298 nm, and the value of $D_{90}$=625 nm.

Table 6 shows the particle diameter distributions of various organic compound powders prepared in Examples 26 to 30 as compared with the particle diameter distributions of the powders before milling.

TABLE 6

| | | Particle diameter distribution (nm) | | | | | | | |
| | | Before milling | | | | After milling | | | |
| | Organic compound | Dav | D10 | D50 | D90 | Dav | D10 | D50 | D90 |
| --- | --- | --- | --- | --- | --- | --- | --- | --- | --- |
| Example 26 | Cur | 16640 | 930 | 12150 | 35870 | 181 | 82 | 144 | 286 |
| Example 27 | Mef | 16130 | 770 | 13290 | 35550 | 205 | 84 | 165 | 328 |
| Example 28 | Ace | 109940 | 41240 | 103460 | 188510 | 186 | 82 | 148 | 296 |
| Example 29 | Ibu | 79030 | 23100 | 69440 | 149660 | 434 | 176 | 335 | 711 |
| Example 30 | Amp | 19660 | 510 | 12520 | 51740 | 376 | 132 | 298 | 625 |

As shown in Table 6, organic compound nano-powder consisting of the particles with so small particle diameter was prepared when organic compound powder was milled with using fructose as one of carbohydrate compounds.

Experiment 8

Milling with Trehalose

Example 31

Preparation of a Curcumin Nano-Powder 100 mg of turmeric powder, 325 mg of trehalose, 50 mg of sucrose fatty acid ester, 9 mg of sodium carboxymethyl cellulose and 110 mg of purified water were served on a glass disk of the foregoing Hoover muller and then kneaded by repeating five times to rotate the disk in 20 turns per time. Above-served contents formed a kind of dough during kneading and whereby the turmeric powder was finely milled 10 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of curcumin nano-powder obtained after above procedures was as follows: $D_{av}$=263 nm, the value of $D_{10}$=86 nm, the value of $D_{50}$=211 nm, and the value of $D_{90}$=444 nm.

Example 32

Preparation of a Mefenamic Acid Nano-Powder

A mefenamic acid powder was milled and then subjected to a dispersion treatment under the same conditions as Example 31 except changing from 100 mg of turmeric powder to 100 mg of mefenamic acid powder. As a result, the particle diameter distribution of mefenamic acid nano-powder obtained after above procedures was as follows: $D_{av}$=193 nm, the value of $D_{10}$=105 nm, the value of $D_{50}$=167 nm, and the value of $D_{90}$=264 nm.

Example 33

Preparation of an Acetaminophen Nano-Powder

The acetaminophen powder was milled under the same conditions as Example 31 except both changing from 100 mg of turmeric powder to 100 mg of acetaminophen powder and changing from sucrose fatty acid ester to decaglyceryl monostearate. Then, 100 mg of the dough obtained after milling was weighed and then subjected to a dispersion treatment under the same conditions as Example 31 except adding only 5 mL of 0.1% sodium dodecylsulfate but no 0.01% hydrogenated soy bean lecithin. As a result, the particle diameter distribution of acetaminophen nano-powder obtained after above procedures was as follows: $D_{av}$=238 nm, the value of $D_{10}$=87 nm, the value of $D_{50}$=196 nm, and the value of $D_{90}$=381 nm.

Example 34

Preparation of an Amphotericin B Nano-Powder

An amphotericin B powder was milled under the same conditions as Example 31 except both changing from 100 mg of turmeric powder to 100 mg of amphotericin B powder and changing from sucrose fatty acid ester to hydrogenated soy bean lecithin. Then, the dough obtained after milling was subjected to a dispersion treatment under the same conditions as Example 31 except adding only 5 mL of 0.1% sodium dodecylsulfate but no 0.01% hydrogenated soy bean lecithin. As a result, the particle diameter distribution of amphotericin B nano-powder obtained after above procedures was as follows: $D_{av}$=162 nm, the value of $D_{10}$=83 nm, the value of $D_{50}$=137 nm, and the value of $D_{90}$=229 nm.

Table 7 shows the particle diameter distributions of various organic compound powders prepared in Examples 31 to 34 as compared with the particle diameter distributions of the powders before milling.

TABLE 7

| | Organic compound | Particle diameter distribution (nm) | | | | | | | |
|---|---|---|---|---|---|---|---|---|---|
| | | Before milling | | | | After milling | | | |
| | | Dav | D10 | D50 | D90 | Dav | D10 | D50 | D90 |
| Example 31 | Cur | 16640 | 930 | 12150 | 35870 | 263 | 86 | 211 | 444 |
| Example 32 | Mef | 16130 | 770 | 13290 | 35550 | 193 | 105 | 167 | 264 |
| Example 33 | Ace | 109940 | 41240 | 103460 | 188510 | 238 | 87 | 196 | 381 |
| Example 34 | Amp | 19660 | 510 | 12520 | 51740 | 162 | 83 | 137 | 229 |

As shown in Table 7, organic compound nano-powder consisting of the particles with so small particle diameter was prepared when organic compound powder was milled with using trehalose as one of carbohydrate compounds.

Experiment 9

Milling with Various Carbohydrate Compounds (1) Milling of a Curcumin Powder

Example 35

Carbohydrate Compound: D-Mannitol

Example 35 is same one as Example 7. The particle diameter distribution of curcumin nano-powder obtained in Example 35 was as follows: $D_{av}$=384 nm, the value of $D_{10}$=154 nm, the value of $D_{50}$=280 nm, and the value of $D_{90}$=569 nm.

Example 36

Carbohydrate Compound: Maltitol

A curcumin powder was milled and then subjected to a dispersion treatment under the same conditions as Example 35 except using maltitol as the carbohydrate compound. As a result, the particle diameter distribution of curcumin nano-powder obtained after above procedures was as follows: $D_{av}$=199 nm, the value of $D_{10}$=95 nm, the value of $D_{50}$=176 nm, and the value of $D_{90}$=286 nm.

Example 37

Carbohydrate Compound: Erythritol

A curcumin powder was milled and then subjected to a dispersion treatment under the same conditions as Example 35 except using erythritol as the carbohydrate compound. As a result, the particle diameter distribution of curcumin nano-powder obtained after above procedures was as follows: $D_{av}$=275 nm, the value of $D_{10}$=98 nm, the value of $D_{50}$=201 nm, and the value of $D_{90}$=483 nm.

Example 38

Carbohydrate Compound: Xylitol

Example 38 is same one as Example 17. The particle diameter distribution of curcumin nano-powder obtained in Example 38 was as follows: $D_{av}$=283 nm, the value of $D_{10}$=138 nm, the value of $D_{50}$=234 nm, and the value of $D_{90}$=418 nm.

Example 39

Carbohydrate Compound: Glucose

Example 39 is same one as Example 22. The particle diameter distribution of curcumin nano-powder obtained in Example 39 was as follows: $D_{av}$=345 nm, the value of $D_{10}$=96 nm, the value of $D_{50}$=242 nm, and the value of $D_{90}$=648 nm.

Example 40

Carbohydrate Compound: Fructose

Example 40 is same one as Example 26. The particle diameter distribution of curcumin nano-powder obtained in Example 40 was as follows: $D_{av}$=181 nm, the value of $D_{10}$=82 nm, the value of $D_{50}$=144 nm, and the value of $D_{90}$=286 nm.

Example 41

Carbohydrate Compound: Lactose Monohydrate

A curcumin powder was milled and then subjected to a dispersion treatment under the same conditions as Example 35 except using lactose monohydrate as the carbohydrate compound. As a result, the particle diameter distribution of curcumin nano-powder obtained after above procedures was as follows: $D_{av}$=320 nm, the value of $D_{10}$=102 nm, the value of $D_{50}$=232 nm, and the value of $D_{90}$=574 nm.

Example 42

Carbohydrate Compound: Trehalose

Example 42 is same one as Example 31. The particle diameter distribution of curcumin nano-powder obtained in Example 42 was as follows: $D_{av}$=263 nm, the value of $D_{10}$=86 nm, the value of $D_{50}$=211 nm, and the value of $D_{90}$=444 nm.

Example 43

Carbohydrate Compound: Cellobiose

A curcumin powder was milled and then subjected to a dispersion treatment under the same conditions as Example 35 except using cellobiose as the carbohydrate compound. As a result, the particle diameter distribution of curcumin nano-powder obtained after above procedures was as follows: $D_{av}$=273 nm, the value of $D_{10}$=41 nm, the value of $D_{50}$=241 nm, and the value of $D_{90}$=435 nm.

(2) Milling of a Mefenamic Acid Powder

Example 44

Carbohydrate Compound: D-Mannitol

Example 44 is same one as Example 8. The particle diameter distribution of mefenamic acid nano-powder obtained in Example 44 was as follows: $D_{av}$=247 nm, the value of $D_{10}$=99 nm, the value of $D_{50}$=198 nm, and the value of $D_{90}$=403 nm.

Example 45

Carbohydrate Compound: Maltitol

A mefenamic acid powder was milled and then subjected to a dispersion treatment under the same conditions as Example 44 except using maltitol as the carbohydrate compound. As a result, the particle diameter distribution of mefenamic acid nano-powder obtained after above procedures was as follows: $D_{av}$=209 nm, the value of $D_{10}$=115 nm, the value of $D_{50}$=185 nm, and the value of $D_{90}$=284 nm.

Example 46

Carbohydrate Compound: Erythritol

A mefenamic acid powder was milled and then subjected to a dispersion treatment under the same conditions as Example 44 except using erythritol as the carbohydrate compound. As a result, the particle diameter distribution of mefenamic acid nano-powder obtained after above procedures was as follows: $D_{av}$=185 nm, the value of $D_{10}$=119 nm, the value of $D_{50}$=164 nm, and the value of $D_{90}$=230 nm.

Example 47

Carbohydrate Compound: Xylitol

Example 47 is same one as Example 18. The particle diameter distribution of mefenamic acid nano-powder obtained in Example 47 was as follows: $D_{av}$=241 nm, the value of $D_{10}$=98 nm, the value of $D_{50}$=191 nm, and the value of $D_{90}$=398 nm.

Example 48

Carbohydrate Compound: Glucose

Example 48 is same one as Example 23. The particle diameter distribution of mefenamic acid nano-powder obtained in Example 48 was as follows: $D_{av}$=224 nm, the value of $D_{10}$=85 nm, the value of $D_{50}$=193 nm, and the value of $D_{90}$=339 nm.

Example 49

Carbohydrate Compound: Fructose

Example 49 is same one as Example 27. The particle diameter distribution of mefenamic acid nano-powder obtained in Example 49 was as follows: $D_{av}$=205 nm, the value of $D_{10}$=84 nm, the value of $D_{50}$=165 nm, and the value of $D_{90}$=328 nm.

Example 50

Carbohydrate Compound: Lactose Monohydrate

A mefenamic acid powder was milled and then subjected to a dispersion treatment under the same conditions as Example 44 except using lactose monohydrate as the carbohydrate compound. As a result, the particle diameter distribution of mefenamic acid nano-powder obtained after above procedures was as follows: $D_{av}$=261 nm, the value of $D_{10}$=114 nm, the value of $D_{50}$=207 nm, and the value of $D_{90}$=417 nm.

Example 51

Carbohydrate Compound: Trehalose

Example 51 is same one as Example 32. The particle diameter distribution of mefenamic acid nano-powder obtained in Example 51 was as follows: $D_{av}$=193 nm, the value of $D_{10}$=105 nm, the value of $D_{50}$=167 nm, and the value of $D_{90}$=264 nm.

Example 52

Carbohydrate Compound: Cellobiose

A mefenamic acid powder was milled and then subjected to a dispersion treatment under the same conditions as Example 44 except using cellobiose as the carbohydrate compound. As a result, the particle diameter distribution of mefenamic acid nano-powder obtained after above procedures was as follows: $D_{av}$=271 nm, the value of $D_{10}$=122 nm, the value of $D_{50}$=217 nm, and the value of $D_{90}$=424 nm.

Example 53

Carbohydrate Compound: Inositol

A mefenamic acid powder was milled and then subjected to a dispersion treatment under the same conditions as Example 44 except using inositol as the carbohydrate compound. As a result, the particle diameter distribution of mefenamic acid nano-powder obtained after above procedures was as follows: $D_{av}$=223 nm, the value of $D_{10}$=101 nm, the value of $D_{50}$=183 nm, and the value of $D_{90}$=341 nm.

Tables 8 and 9 show the particle diameter distributions of various organic compound powders prepared in Examples 35 to 43 and Examples 44 to 53, respectively as compared with the particle diameter distributions of the powders before milling. The term "Man" in the tables means D-mannitol. The term "Mal" in the tables means maltitol. The term "Ery" in the tables means erythritol. The term "Xyl" in the tables means xylitol. The term "Glu" in the tables means glucose. The term "Fru" in the tables means fructose. The term "Lac" in the tables means lactose. The term "Tre" in the tables means trehalose. The term "Cel" in the tables means cellobiose. The term "Ino" in the tables means inositol. These definitions shall apply to following tables.

TABLE 8

| Carbo-hydrate com-pound | Particle diameter distribution (nm) | | | | | | | |
|---|---|---|---|---|---|---|---|---|
| | Before milling | | | | After milling | | | |
| | Dav | D10 | D50 | D90 | Dav | D10 | D50 | D90 |
| Example 35 | Man | 16640 | 930 | 12150 | 35870 | 384 | 154 | 280 | 569 |
| Example 36 | Mal | | | | | 199 | 95 | 176 | 286 |
| Example 37 | Ery | | | | | 275 | 98 | 201 | 483 |
| Example 38 | Xyl | | | | | 283 | 138 | 234 | 418 |
| Example 39 | Glu | | | | | 345 | 96 | 242 | 648 |
| Example 40 | Fru | | | | | 181 | 82 | 144 | 286 |
| Example 41 | Lac | | | | | 320 | 102 | 232 | 574 |
| Example 42 | Tre | | | | | 263 | 86 | 211 | 444 |
| Example 43 | Cel | | | | | 273 | 41 | 241 | 435 |

TABLE 9

| Carbo-hydrate com-pound | Particle diameter distribution (nm) | | | | | | | |
|---|---|---|---|---|---|---|---|---|
| | Before milling | | | | After milling | | | |
| | Dav | D10 | D50 | D90 | Dav | D10 | D50 | D90 |
| Example 44 | Man | 16130 | 770 | 13290 | 35550 | 247 | 99 | 198 | 403 |
| Example 45 | Mal | | | | | 209 | 115 | 185 | 284 |
| Example 46 | Ery | | | | | 185 | 119 | 164 | 230 |
| Example 47 | Xyl | | | | | 241 | 98 | 191 | 398 |
| Example 48 | Glu | | | | | 224 | 85 | 193 | 339 |
| Example 49 | Fru | | | | | 205 | 84 | 165 | 328 |
| Example 50 | Lac | | | | | 261 | 114 | 207 | 417 |
| Example 51 | Tre | | | | | 193 | 105 | 167 | 264 |
| Example 52 | Cel | | | | | 271 | 122 | 217 | 424 |
| Example 53 | Ino | | | | | 223 | 101 | 183 | 341 |

As shown in Tables 8 and 9, organic compound nano-powder consisting of the particles with so small particle diameter was prepared even when organic compound powder was milled with using the sugar alcohol like mannitol, maltitol, erythritol or xylitol; the monosaccharide like inositol, glucose or fructose; or the disaccharide like lactose, trehalose or cellobiose.

Experiment 10

Milling with a Mixture of Carbohydrate Compounds (1) Milling of a Curcumin Powder

Example 54

Mixture Group: D-Mannitol and Sorbitol 100 mg of turmeric powder, a mixed carbohydrate compound of 162.5 mg of D-(−)-mannitol and 162.5 mg of sorbitol (mass ratio=1:1), 50 mg of sucrose fatty acid ester, 9 mg of sodium carboxymethyl cellulose and 110 mg of purified water were served on a glass disk of the foregoing Hoover muller and then kneaded by repeating five times to rotate the disk in 20 turns per time. Above-served contents formed a kind of dough during kneading and whereby the turmeric powder was finely milled 10 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of curcumin nano-powder obtained after above procedures was as follows: $D_{av}=421$ nm, the value of $D_{10}=80$ nm, the value of $D_{50}=199$ nm, and the value of $D_{90}=685$ nm.

Example 55

Mixture Group: D-Mannitol and Xylitol

A curcumin powder was milled and then subjected to a dispersion treatment under the same conditions as Example 54 except using a mixed carbohydrate compound of 162.5 mg of D-(−)-mannitol and 162.5 mg of xylitol (mass ratio=1:1) instead of the mixed carbohydrate compound of 162.5 mg of D-(−)-mannitol and 162.5 mg of sorbitol (mass ratio=1:1). As a result, the particle diameter distribution of curcumin nano-powder obtained after above procedures was as follows: $D_{av}=237$ nm, the value of $D_{10}=98$ nm, the value of $D_{50}=183$ nm, and the value of $D_{90}=394$ nm.

Example 56

Mixture Group: D-Mannitol and Dextrin

A curcumin powder was milled and then subjected to a dispersion treatment under the same conditions as Example 54 except using a mixed carbohydrate compound of 162.5 mg of D-(−)-mannitol and 162.5 mg of dextrin (mass ratio=1:1) instead of the mixed carbohydrate compound of 162.5 mg of D-(−)-mannitol and 162.5 mg of sorbitol (mass ratio=1:1). As a result, the particle diameter distribution of curcumin nano-powder obtained after above procedures was as follows: $D_{av}=254$ nm, the value of $D_{10}=83$ nm, the value of $D_{50}=189$ nm, and the value of $D_{90}=454$ nm.

(1) Milling of a Mefenamic Acid Powder

Example 57

Mixture Group: D-Mannitol and Sorbitol

The processes of milling and dispersion treatment were performed under the same conditions as Example 54 except using a mefenamic acid powder instead of the curcumin powder. As a result, the particle diameter distribution of mefenamic acid nano-powder obtained after above procedures was as follows: $D_{av}=365$ nm, the value of $D_{10}=127$ nm, the value of $D_{50}=239$ nm, and the value of $D_{90}=518$ nm.

Example 58

Mixture Group: D-Mannitol and Xylitol

The processes of milling and dispersion treatment were performed under the same conditions as Example 55 except using a mefenamic acid powder instead of the curcumin powder. As a result, the particle diameter distribution of mefenamic acid nano-powder obtained after above procedures was as follows: $D_{av}=226$ nm, the value of $D_{10}=105$ nm, the value of $D_{50}=182$ nm, and the value of $D_{90}=350$ nm.

Example 59

Mixture Group: D-Mannitol and Dextrin

The processes of milling and dispersion treatment were performed under the same conditions as Example 56 except using a mefenamic acid powder instead of the curcumin powder. As a result, the particle diameter distribution of mefenamic acid nano-powder obtained after above procedures was as follows: $D_{av}=238$ nm, the value of $D_{10}=123$ nm, the value of $D_{50}=193$ nm, and the value of $D_{90}=351$ nm.

Tables 10 and 11 show the particle diameter distributions of various organic compound powders prepared in Examples 54 to 56 and Examples 57 to 59, respectively as compared with the particle diameter distributions of the powders before milling. The term "Sor" in the tables means sorbitol. The term "Dext" in the tables means dextrin.

TABLE 10

| | | | Particle diameter distribution (nm) | | | | | | | |
| | Carbohydrate | Organic | Before milling | | | | After milling | | | |
| | compound | compound | Dav | D10 | D50 | D90 | Dav | D10 | D50 | D90 |
| Example 54 | Man + Sor | Cur | 16640 | 930 | 12150 | 35870 | 421 | 80 | 199 | 685 |
| Example 55 | Man + Xyl | | | | | | 237 | 98 | 183 | 394 |
| Example 56 | Man + Dext | | | | | | 254 | 83 | 189 | 454 |

TABLE 11

| | Carbohydrate compound | Organic compound | Particle diameter distribution (nm) | | | | | | | |
|---|---|---|---|---|---|---|---|---|---|---|
| | | | Before milling | | | | After milling | | | |
| | | | Dav | D10 | D50 | D90 | Day | D10 | D50 | D90 |
| Example 57 | Man + Sor | Mef | 16130 | 770 | 13290 | 35550 | 365 | 127 | 239 | 518 |
| Example 58 | Man + Xyl | | | | | | 226 | 105 | 182 | 350 |
| Example 59 | Man + Dext | | | | | | 238 | 123 | 193 | 351 |

As shown in Tables 10 and 11, with regard to the milling capacity of the carbohydrate compound, the mixture system of mannitol and xylitol or the mixture system of mannitol and dextrin was more advantageous than the mixture system of mannitol and sorbitol.

Experiment 11

Milling with a Mixture of Carbohydrate Compound and Salt

Various organic compounds were milled with a mixture of carbohydrate compound and salt.

(1) Preparation of an Indomethacin Nano-Powder

Example 60

An indomethacin powder was milled with using a mixture of carbohydrate compound and salt which was in a mass ratio of D-mannitol:sodium chloride=6:1 and a hydrogenated soy bean lecithin under following conditions.

100 mg of indomethacin powder, 600 mg of D-(−)-mannitol, 100 mg of sodium chloride (trade name of Tomita salt K30, manufactured by Tomita Pharmaceutical Co., Ltd.), 30 mg of polyvinylpyrrolidone, 50 mg of hydrogenated soy bean lecithin and 200 mg of glycerin were served on a glass disk of the foregoing Hoover muller and then kneaded by repeating five times to rotate the disk in 20 turns per time. Above-served contents formed a kind of dough during kneading and whereby the indomethacin powder was finely milled 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of indomethacin nano-powder obtained after above procedures was as follows: $D_{av}$=283 nm, the value of $D_{10}$=104 nm, the value of $D_{50}$=204 nm, and the value of $D_{90}$=500 nm.

Example 61

An indomethacin powder was milled and then subjected to a dispersion treatment under the same conditions as Example 60 except using only a mixture of carbohydrate compound and salt which was in a mass ratio of D-mannitol:sodium chloride=6:1 and no hydrogenated soy bean lecithin. As a result, the particle diameter distribution of indomethacin nano-powder obtained after above procedures was as follows: $D_{av}$=253 nm, the value of $D_{10}$=98 nm, the value of $D_{50}$=189 nm, and the value of $D_{90}$=432 nm.

Example 62

An indomethacin powder was milled and then subjected to a dispersion treatment under the same conditions as Example 60 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of indomethacin nano-powder obtained after above procedures was as follows: $D_{av}$=340 nm, the value of $D_{10}$=171 nm, the value of $D_{50}$=296 nm, and the value of $D_{90}$=474 nm.

Example 63

An indomethacin powder was milled and then subjected to a dispersion treatment under the same conditions as Example 61 except using only a mixture of carbohydrate compound and salt which was in a mass ratio of D-mannitol:sodium chloride=1:1 (350 mg of D-(−)-mannitol and 350 mg of sodium chloride) and no hydrogenated soy bean lecithin. As a result, the particle diameter distribution of indomethacin nano-powder obtained after above procedures was as follows: $D_{av}$=255 nm, the value of $D_{10}$=100 nm, the value of $D_{50}$=199 nm, and the value of $D_{90}$=419 nm.

(2) Preparation of a Felbinac Nano-Powder

Example 64

A felbinac powder was milled with using a mixture of carbohydrate compound and salt which was in a mass ratio of D-mannitol:sodium chloride=6:1 and a hydrogenated soy bean lecithin under following conditions.

100 mg of felbinac powder (same as used in Example 14 and also used in following experiments), 600 mg of D-(−)-mannitol, 100 mg of sodium chloride (same as used in Example 60 and also used in following experiments), 30 mg of polyvinylpyrrolidone, 50 mg of hydrogenated soy bean lecithin and 200 mg of glycerin were served on a glass disk of the foregoing Hoover muller and then kneaded by repeating five times to rotate the disk in 20 turns per time. Above-served contents formed a kind of dough during kneading and whereby the felbinac powder was finely milled. 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of felbinac nano-powder obtained after above procedures was as follows: $D_{av}$=246 nm, the value of $D_{10}$=137 nm, the value of $D_{50}$=212 nm, and the value of $D_{90}$=330 nm.

Example 65

A felbinac powder was milled and then subjected to a dispersion treatment under the same conditions as Example 64 except using only a mixture of carbohydrate compound and salt which was in a mass ratio of D-mannitol:sodium chloride=6:1 and no hydrogenated soy bean lecithin. As a result, the particle diameter distribution of felbinac nano-powder obtained after above procedures was as follows: $D_{av}$=228 nm, the value of $D_{10}$=105 nm, the value of $D_{50}$=186 nm, and the value of $D_{90}$=349 nm.

Example 66

A felbinac powder was milled and then subjected to a dispersion treatment under the same conditions as Example 64 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of felbinac nano-powder obtained after above procedures was as follows: $D_{av}$=211 nm, the value of $D_{10}$=115 nm, the value of $D_{50}$=181 nm, and the value of $D_{90}$=292 nm.

Example 67

A felbinac powder was milled and then subjected to a dispersion treatment under the same conditions as Example 65 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of felbinac nano-powder obtained after above procedures was as follows: $D_{av}$=228 nm, the value of $D_{10}$=126 nm, the value of $D_{50}$=199 nm, and the value of $D_{90}$=305 nm.

(3) Preparation of a Pranlukast Hydrate Nano-Powder

Example 68

A pranlukast hydrate powder was milled with using a mixture of carbohydrate compound and salt which was in a mass ratio of D-mannitol:sodium chloride=6:1 and a hydrogenated soy bean lecithin under following conditions.

100 mg of pranlukast hydrate powder, 600 mg of D-(−)-mannitol, 100 mg of sodium chloride, 30 mg of polyvinylpyrrolidone, 50 mg of hydrogenated soy bean lecithin and 200 mg of glycerin were served on a glass disk of the foregoing Hoover muller and then kneaded by repeating five times to rotate the disk in 20 turns per time. Above-served contents formed a kind of dough during kneading and whereby the pranlukast hydrate powder was finely milled. 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of pranlukast hydrate nano-powder obtained after above procedures was as follows: $D_{av}$=151 nm, the value of $D_{10}$=60 nm, the value of $D_{50}$=116 nm, and the value of $D_{90}$=253 nm.

Example 69

A pranlukast hydrate powder was milled and then subjected to a dispersion treatment under the same conditions as Example 68 except using only a mixture of carbohydrate compound and salt which was in a mass ratio of D-mannitol:sodium chloride=6:1 and no hydrogenated soy bean lecithin. As a result, the particle diameter distribution of pranlukast hydrate nano-powder obtained after above procedures was as follows: $D_{av}$=195 nm, the value of $D_{10}$=56 nm, the value of $D_{50}$=152 nm, and the value of $D_{90}$=345 nm.

Example 70

A pranlukast hydrate powder was milled and then subjected to a dispersion treatment under the same conditions as Example 68 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of pranlukast hydrate nano-powder obtained after above procedures was as follows: $D_{av}$=192 nm, the value of $D_{10}$=90 nm, the value of $D_{50}$=158 nm, and the value of $D_{90}$=295 nm.

Example 71

A pranlukast hydrate powder was milled and then subjected to a dispersion treatment under the same conditions as Example 69 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of pranlukast hydrate nano-powder obtained after above procedures was as follows: $D_{av}$=204 nm, the value of $D_{10}$=81 nm, the value of $D_{50}$=166 nm, and the value of $D_{90}$=326 nm.

(4) Preparation of a Dexamethasone Nano-Powder

Example 72

A dexamethasone powder was milled with using a mixture of carbohydrate compound and salt which was in a mass ratio of D-mannitol:sodium chloride=6:1 and a hydrogenated soy bean lecithin under following conditions.

100 mg of dexamethasone powder, 600 mg of D-(−)-mannitol, 100 mg of sodium chloride, 30 mg of polyvinylpyrrolidone, 50 mg of hydrogenated soy bean lecithin and 200 mg of glycerin were served on a glass disk of the foregoing Hoover muller and then kneaded by repeating five times to rotate the disk in 20 turns per time. Above-served contents formed a kind of dough during kneading and whereby the dexamethasone powder was finely milled. 20 mg of the dough obtained after milling was weighed into a 50-mL glass vial and then added 5 mL of Polyoxyethylene Hydrogenated Castor Oil 60 (NIKKOL HCO-60, manufactured by Nikko Chemicals Co., Ltd.). Then, the solution obtained above was subjected to a dispersion treatment by using the foregoing bath-type ultrasonic disperser for 1 to 2 minutes. As a result, the particle diameter distribution of dexamethasone nano-powder obtained after above procedures was as follows: $D_{av}$=217 nm, the value of $D_{10}$=74 nm, the value of $D_{50}$=158 nm, and the value of $D_{90}$=389 nm.

Example 73

A dexamethasone powder was milled and then subjected to a dispersion treatment under the same conditions as Example 72 except using only a mixture of carbohydrate compound and salt which was in a mass ratio of D-mannitol:sodium chloride=6:1 and no hydrogenated soy bean lecithin. As a result, the particle diameter distribution of dexamethasone nano-powder obtained after above procedures was as follows:

$D_{av}$=168 nm, the value of $D_{10}$=82 nm, the value of $D_{50}$=149 nm, and the value of $D_{90}$=240 nm.

Example 74

A dexamethasone powder was milled and then subjected to a dispersion treatment under the same conditions as Example 72 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of dexamethasone nano-powder obtained after above procedures was as follows: $D_{av}$=205 nm, the value of $D_{10}$=75 nm, the value of $D_{50}$=166 nm, and the value of $D_{90}$=336 nm.

Example 75

A dexamethasone powder was milled and then subjected to a dispersion treatment under the same conditions as Example 73 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of dexamethasone nano-powder obtained after above procedures was as follows: $D_{av}$=185 nm, the value of $D_{10}$=108 nm, the value of $D_{50}$=162 nm, and the value of $D_{90}$=243 nm.

(5) Preparation of a Fenofibrate Nano-Powder

Example 76

A fenofibrate powder was milled with using a mixture of carbohydrate compound and salt which was in a mass ratio of D-mannitol:sodium chloride=6:1 and a hydrogenated soy bean lecithin under following conditions.

100 mg of fenofibrate powder (manufactured by Sigma-Aldrich Corporation, $D_{av}$: 48170 nm, the value of $D_{10}$: 3520 nm, the value of $D_{50}$: 33720 nm, and the value of $D_{90}$: 115590 nm), 600 mg of D-(−)-mannitol, 100 mg of sodium chloride, 30 mg of polyvinylpyrrolidone, 50 mg of hydrogenated soy bean lecithin and 200 mg of glycerin were served on a glass disk of the foregoing Hoover muller and then kneaded by repeating five times to rotate the disk in 20 turns per time. Above-served contents formed a kind of dough during kneading and whereby the fenofibrate powder was finely milled 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of fenofibrate nano-powder obtained after above procedures was as follows: $D_{av}$=320 nm, the value of $D_{10}$=149 nm, the value of $D_{50}$=265 nm, and the value of $D_{90}$=474 nm.

Example 77

A fenofibrate powder was milled and then subjected to a dispersion treatment under the same conditions as Example 76 except using only a mixture of carbohydrate compound and salt which was in a mass ratio of D-mannitol:sodium chloride=6:1 and no hydrogenated soy bean lecithin. As a result, the particle diameter distribution of fenofibrate nano-powder obtained after above procedures was as follows: $D_{av}$=269 nm, the value of $D_{10}$=132 nm, the value of $D_{50}$=223 nm, and the value of $D_{90}$=397 nm.

Example 78

A fenofibrate powder was milled and then subjected to a dispersion treatment under the same conditions as Example 76 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of fenofibrate nano-powder obtained after above procedures was as follows: $D_{av}$=368 nm, the value of $D_{10}$=182 nm, the value of $D_{50}$=298 nm, and the value of $D_{90}$=547 nm.

Example 79

A fenofibrate powder was milled and then subjected to a dispersion treatment under the same conditions as Example 77 except using a mixture of carbohydrate compound and salt which was in a mass ratio of D-mannitol:sodium chloride=1:1 (350 mg of D-(−)-mannitol and 350 mg of sodium chloride). As a result, the particle diameter distribution of fenofibrate nano-powder obtained after above procedures was as follows: $D_{av}$=311 nm, the value of $D_{10}$=172 nm, the value of $D_{50}$=264 nm, and the value of $D_{90}$=427 nm.

Table 12 shows the particle diameter distributions of various organic compound powders prepared in Examples 60 to 79. The term "Fen" in the table means fenofibrate.

TABLE 12

| | Organic compound | Carbohydrate compound | Salt | Carbohydrate:Salt | hydrogenated soy bean lecithin | Particle diameter distribution (nm) | | | | | | | |
|---|---|---|---|---|---|---|---|---|---|---|---|---|---|
| | | | | | | Before milling | | | | After milling | | | |
| | | | | | | Dav | D10 | D50 | D90 | Dav | D10 | D50 | D90 |
| Example 60 | Ind | Man | NaCl | 6:1 | Exist | 12400 | 630 | 8670 | 30820 | 283 | 104 | 204 | 500 |
| Example 61 | | | | | No | | | | | 253 | 98 | 189 | 432 |
| Example 62 | | | | 1:1 | Exist | | | | | 340 | 171 | 296 | 474 |
| Example 63 | | | | | No | | | | | 255 | 100 | 199 | 419 |
| Example 64 | Fel | Man | NaCl | 6:1 | Exist | 190720 | 46270 | 166710 | 356860 | 246 | 137 | 212 | 330 |
| Example 65 | | | | | No | | | | | 228 | 105 | 186 | 349 |
| Example 66 | | | | 1:1 | Exsist | | | | | 211 | 115 | 181 | 292 |
| Example 67 | | | | | No | | | | | 228 | 126 | 199 | 305 |
| Example 68 | Pra | Man | NaCl | 6:1 | Exist | 9500 | 1050 | 6150 | 23660 | 151 | 60 | 116 | 253 |
| Example 69 | | | | | No | | | | | 195 | 56 | 152 | 345 |
| Example 70 | | | | 1:1 | Exist | | | | | 192 | 90 | 158 | 295 |
| Example 71 | | | | | No | | | | | 204 | 81 | 166 | 326 |
| Example 72 | Dex | Man | NaCl | 6:1 | Exist | 2690 | 280 | 2580 | 5360 | 217 | 74 | 158 | 389 |
| Example 73 | | | | | No | | | | | 168 | 82 | 149 | 240 |

TABLE 12-continued

| | | | | hydrogenated | Particle diameter distribution (nm) | | | | | | | |
|---|---|---|---|---|---|---|---|---|---|---|---|---|
| | | | | soy bean | Before milling | | | | After milling | | | |
| Organic compound | Carbohydrate compound | Salt | Carbohydrate:Salt | lecithin | Dav | D10 | D50 | D90 | Dav | D10 | D50 | D90 |
| Example 74 | | | 1:1 | Exist | | | | | 205 | 75 | 166 | 336 |
| Example 75 | | | | No | | | | | 185 | 108 | 162 | 243 |
| Example 76 | Fen | Man | NaCl | 6:1 | Exist | 48170 | 3520 | 33720 | 115590 | 320 | 149 | 265 | 474 |
| Example 77 | | | | | No | | | | | 269 | 132 | 223 | 397 |
| Example 78 | | | | 1:1 | Exist | | | | | 368 | 182 | 298 | 547 |
| Example 79 | | | | | No | | | | | 311 | 172 | 264 | 427 |

As shown in Table 12, the diameter distributions of nano-powders obtained after milling various organic compounds were almost same one in spite of changing the mass ratio of the carbohydrate compound and the salt, or the presence or absence of lecithin.

Experiment 12

Milling without Anti-Agglomeration Agent

Various organic compounds were milled with carbohydrate compound and polyol, further with salt optionally.

(1) Preparation of an Indomethacin Nano-Powder

Example 80

100 mg of indomethacin powder, 600 mg of D-(−)-mannitol, 100 mg of sodium chloride and 200 mg of glycerin were served on a glass disk of the foregoing Hoover muller and then kneaded by repeating five times to rotate the disk in 20 turns per time. Above-served contents formed a kind of dough during kneading and whereby the indomethacin powder was finely milled. 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of indomethacin nano-powder obtained after above procedures was as follows: $D_{av}$=335 nm, the value of $D_{10}$=115 nm, the value of $D_{50}$=237 nm, and the value of $D_{90}$=609 nm.

Example 81

An indomethacin powder was milled and then subjected to a dispersion treatment under the same conditions as Example 80 except using 350 mg of D-(−)-mannitol and 350 mg of sodium chloride. As a result, the particle diameter distribution of indomethacin nano-powder obtained after above procedures was as follows: $D_{av}$=243 nm, the value of $D_{10}$=132 nm, the value of $D_{50}$=209 nm, and the value of $D_{90}$=332 nm.

Example 82

An indomethacin powder was milled and then subjected to a dispersion treatment under the same conditions as Example 80 except using 700 mg of D-(−)-mannitol and no sodium chloride. As a result, the particle diameter distribution of indomethacin nano-powder obtained after above procedures was as follows: $D_{av}$=283 nm, the value of $D_{10}$=128 nm, the value of $D_{50}$=231 nm, and the value of $D_{90}$=433 nm.

(1) Preparation of a Felbinac Nano-Powder

Example 83

100 mg of felbinac powder, 600 mg of D-(−)-mannitol, 100 mg of sodium chloride and 200 mg of glycerin were served on a glass disk of the foregoing Hoover muller and then kneaded by repeating five times to rotate the disk in 20 turns per time. Above-served contents formed a kind of dough during kneading and whereby the felbinac powder was finely milled. 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of felbinac nano-powder obtained after above procedures was as follows: $D_{av}$=415 nm, the value of $D_{10}$=236 nm, the value of $D_{50}$=360 nm, and the value of $D_{90}$=588 nm.

Example 84

A felbinac powder was milled and then subjected to a dispersion treatment under the same conditions as Example 83 except using 350 mg of D-(−)-mannitol and 350 mg of sodium chloride. As a result, the particle diameter distribution of felbinac nano-powder obtained after above procedures was as follows: $D_{av}$=479 nm, the value of $D_{10}$=257 nm, the value of $D_{50}$=414 nm, and the value of $D_{90}$=690 nm.

Example 85

A felbinac powder was milled and then subjected to a dispersion treatment under the same conditions as Example 83 except using 700 mg of D-(−)-mannitol and no sodium chloride. As a result, the particle diameter distribution of felbinac nano-powder obtained after above procedures was as follows: $D_{av}$=488 nm, the value of $D_{10}$=242 nm, the value of $D_{50}$=410 nm, and the value of $D_{90}$=744 nm.

(3) Preparation of a Pranlukast Hydrate Nano-Powder

Example 86

100 mg of pranlukast hydrate powder, 600 mg of D-(−)-mannitol, 100 mg of sodium chloride and 200 mg of glycerin were served on a glass disk of the foregoing Hoover muller and then kneaded by repeating five times to rotate the disk in 20 turns per time. Above-served contents formed a kind of dough during kneading and whereby the pranlukast hydrate powder was finely milled 10 mg of the dough obtained after milling was weighed into a 50-mL glass vial and then added 10 mL of 0.1% Polyoxyethylene Hydrogenated Castor Oil 60. Then, the solution obtained above was subjected to a dispersion treatment by using the foregoing bath-type ultrasonic disperser for 1 to 2 minutes. As a result, the particle diameter distribution of pranlukast hydrate nano-powder obtained after above procedures was as follows: $D_{av}$=286 nm, the value of $D_{10}$=95 nm, the value of $D_{50}$=171 nm, and the value of $D_{90}$=327 nm.

Example 87

A pranlukast hydrate powder was milled and then subjected to a dispersion treatment under the same conditions as Example 86 except using 350 mg of D-(-)-mannitol and 350 mg of sodium chloride. As a result, the particle diameter distribution of pranlukast hydrate nano-powder obtained after above procedures was as follows: $D_{av}$=190 nm, the value of $D_{10}$=93 nm, the value of $D_{50}$=158 nm, and the value of $D_{90}$=282 nm.

Example 88

A pranlukast hydrate powder was milled and then subjected to a dispersion treatment under the same conditions as Example 86 except using 700 mg of D-(-)-mannitol and no sodium chloride. As a result, the particle diameter distribution of pranlukast hydrate nano-powder obtained after above procedures was as follows: $D_{av}$=188 nm, the value of $D_{10}$=100 nm, the value of $D_{50}$=159 nm, and the value of $D_{90}$=265 nm.

(4) Preparation of a Dexamethasone Nano-Powder

Example 89

100 mg of dexamethasone powder, 600 mg of D-(-)-mannitol, 100 mg of sodium chloride and 200 mg of glycerin were served on a glass disk of the foregoing Hoover muller and then kneaded by repeating five times to rotate the disk in 20 turns per time. Above-served contents formed a kind of dough during kneading and whereby the dexamethasone powder was finely milled 20 mg of the dough obtained after milling was weighed into a 50-mL glass vial and then added 5 mL of 0.1% Polyoxyethylene Hydrogenated Castor Oil 60. Then, the solution obtained above was subjected to a dispersion treatment by using the foregoing bath-type ultrasonic disperser for 1 to 2 minutes. As a result, the particle diameter distribution of dexamethasone nano-powder obtained after above procedures was as follows: $D_{av}$=221 nm, the value of $D_{10}$=114 nm, the value of $D_{50}$=185 nm, and the value of $D_{90}$=318 nm.

Example 90

A dexamethasone powder was milled and then subjected to a dispersion treatment under the same conditions as Example 89 except using 350 mg of D-(-)-mannitol and 350 mg of sodium chloride. As a result, the particle diameter distribution of dexamethasone nano-powder obtained after above procedures was as follows: $D_{av}$=227 nm, the value of $D_{10}$=133 nm, the value of $D_{50}$=198 nm, and the value of $D_{90}$=295 nm.

Example 91

A dexamethasone powder was milled and then subjected to a dispersion treatment under the same conditions as Example 89 except using 700 mg of D-(-)-mannitol and no sodium chloride. As a result, the particle diameter distribution of dexamethasone nano-powder obtained after above procedures was as follows: $D_{av}$=270 nm, the value of $D_{10}$=125 nm, the value of $D_{50}$=225 nm, and the value of $D_{90}$=401 nm.

Table 13 shows the particle diameter distributions of various organic compound powders prepared in Examples 80 to 91.

TABLE 13

| | Organic compound | Carbohydrate compound | Salt | Carbohydrate: Salt | Before milling | | | | After milling | | | |
|---|---|---|---|---|---|---|---|---|---|---|---|---|
| | | | | | Dav | D10 | D50 | D90 | Dav | D10 | D50 | D90 |
| Example 80 | Ind | Man | NaCl | 6:1 | 12400 | 630 | 8670 | 30820 | 335 | 115 | 237 | 609 |
| Example 81 | | | | 1:1 | | | | | 243 | 132 | 209 | 332 |
| Example 82 | | | | 1:0 | | | | | 283 | 128 | 231 | 433 |
| Example 83 | Fel | Man | NaCl | 6:1 | 190720 | 46270 | 166710 | 356860 | 415 | 236 | 360 | 588 |
| Example 84 | | | | 1:1 | | | | | 479 | 257 | 414 | 690 |
| Example 85 | | | | 1:0 | | | | | 488 | 242 | 410 | 744 |
| Example 86 | Pra | Man | NaCl | 6:1 | 9500 | 1050 | 6150 | 23660 | 286 | 95 | 171 | 327 |
| Example 87 | | | | 1:1 | | | | | 190 | 93 | 158 | 282 |
| Example 88 | | | | 1:0 | | | | | 188 | 100 | 159 | 265 |
| Example 89 | Dex | Man | NaCl | 6:1 | 2690 | 280 | 2580 | 5360 | 221 | 114 | 185 | 318 |
| Example 90 | | | | 1:1 | | | | | 227 | 133 | 198 | 295 |
| Example 91 | | | | 1:0 | | | | | 270 | 125 | 225 | 401 |

As shown clearly from Table 13, it was achieved to mill the organic compound to nanoscale even without adding any anti-agglomeration agents like lecithin and polyvinylpyrrolidone at the process of milling.

Experiment 13

Milling with Using Various Polyols

An indomethacin powder was milled with adding carbohydrate compound and polyols other than glycerin.

(1) Milling with Ethylene Glycol as Polyol

Example 92

100 mg of indomethacin powder, 700 mg of xylitol and 200 mg of ethylene glycol (manufactured by Wako Pure Chemical Industries, Ltd.) were served on a glass disk of the foregoing Hoover muller and then kneaded by repeating five times to rotate the disk in 20 turns per time. Above-served contents formed a kind of dough during kneading and whereby the indomethacin powder was finely milled. 10 mg of the dough obtained after milling was weighed into a 50-mL glass vial and then added 10 mL of 0.1% sodium dodecylsulfate. Then, the solution obtained above was subjected to a dispersion treatment by using the foregoing bath-type ultrasonic disperser for 1 to 2 minutes. As a result, the particle diameter distribution of indomethacin nano-powder obtained after above procedures was as follows: $D_{av}$=487 nm, the value of $D_{10}$=121 nm, the value of $D_{50}$=204 nm, and the value of $D_{90}$=498 nm.

Example 93

An indomethacin powder was milled and then subjected to a dispersion treatment under the same conditions as Example 92 except using fructose instead of xylitol. As a result, the particle diameter distribution of indomethacin nano-powder obtained after above procedures was as follows: $D_{av}$=261 nm, the value of $D_{10}$=142 nm, the value of $D_{50}$=227 nm, and the value of $D_{90}$=353 nm.

Example 94

An indomethacin powder was milled and then subjected to a dispersion treatment under the same conditions as Example 92 except using trehalose instead of xylitol. As a result, the particle diameter distribution of indomethacin nano-powder obtained after above procedures was as follows: $D_{av}$=420 nm, the value of $D_{10}$=130 nm, the value of $D_{50}$=309 nm, and the value of $D_{90}$=749 nm.

(2) Milling with Propylene Glycol as Polyol

Example 95

An indomethacin powder was milled and then subjected to a dispersion treatment under the same conditions as Example 92 except using propylene glycol (manufactured by Wako Pure Chemical Industries, Ltd. and also used in following experiments) instead of ethylene glycol. As a result, the particle diameter distribution of indomethacin nano-powder obtained after above procedures was as follows: $D_{av}$=217 nm, the value of $D_{10}$=125 nm, the value of $D_{50}$=189 nm, and the value of $D_{90}$=284 nm.

Example 96

An indomethacin powder was milled and then subjected to a dispersion treatment under the same conditions as Example 95 except using fructose instead of xylitol. As a result, the particle diameter distribution of indomethacin nano-powder obtained after above procedures was as follows: $D_{av}$=316 nm, the value of $D_{10}$=118 nm, the value of $D_{50}$=222 nm, and the value of $D_{90}$=497 nm.

Example 97

An indomethacin powder was milled and then subjected to a dispersion treatment under the same conditions as Example 95 except using trehalose instead of xylitol. As a result, the particle diameter distribution of indomethacin nano-powder obtained after above procedures was as follows: $D_{av}$=365 nm, the value of $D_{10}$=158 nm, the value of $D_{50}$=283 nm, and the value of $D_{90}$=598 nm.

(3) Milling with Polyethylene Glycol as Polyol

Example 98

An indomethacin powder was milled and then subjected to a dispersion treatment under the same conditions as Example 92 except using polyethylene glycol 400 (manufactured by Wako Pure Chemical Industries, Ltd. and also used in following experiments) instead of ethylene glycol. As a result, the particle diameter distribution of indomethacin nano-powder obtained after above procedures was as follows: $D_{av}$=456 nm, the value of $D_{10}$=136 nm, the value of $D_{50}$=278 nm, and the value of $D_{90}$=726 nm.

Example 99

An indomethacin powder was milled and then subjected to a dispersion treatment under the same conditions as Example 98 except using fructose instead of xylitol. As a result, the particle diameter distribution of indomethacin nano-powder obtained after above procedures was as follows: $D_{av}$=368 nm, the value of $D_{10}$=145 nm, the value of $D_{50}$=281 nm, and the value of $D_{90}$=616 nm.

Example 100

An indomethacin powder was milled and then subjected to a dispersion treatment under the same conditions as Example 98 except using trehalose instead of xylitol. As a result, the particle diameter distribution of indomethacin nano-powder obtained after above procedures was as follows: $D_{av}$=454 nm, the value of $D_{10}$=151 nm, the value of $D_{50}$=351 nm, and the value of $D_{90}$=776 nm.

Table 14 shows the particle diameter distributions of indomethacin powders prepared in Examples 92 to 100.

TABLE 14

| | | | | Particle diameter distribution (nm) | | | | | | | |
| | | | | Before milling | | | | After milling | | | |
| | Organic compound | Polyol | Carbohydrate compound | Dav | D10 | D50 | D90 | Dav | D10 | D50 | D90 |
|---|---|---|---|---|---|---|---|---|---|---|---|
| Example 92 | Ind | Ethylene glycol | Xyl | 12400 | 630 | 8670 | 30820 | 487 | 121 | 204 | 498 |
| Example 93 | | | Fru | | | | | 261 | 142 | 227 | 353 |
| Example 94 | | | Tre | | | | | 420 | 130 | 309 | 749 |
| Example 95 | | Propylene glycol | Xyl | | | | | 217 | 125 | 189 | 284 |
| Example 96 | | | Fru | | | | | 316 | 118 | 222 | 497 |
| Example 97 | | | Tre | | | | | 365 | 158 | 283 | 598 |
| Example 98 | | Polyethylene glycol 400 | Xyl | | | | | 456 | 136 | 278 | 726 |
| Example 99 | | | Fru | | | | | 368 | 145 | 281 | 616 |
| Example 100 | | | Tre | | | | | 454 | 151 | 351 | 776 |

As shown clearly from Table 14, it was achieved to mill the organic compound to nanoscale even with using polyols other than glycerin.

Experiment 14

Investigation of the Additive Ratio of Carbohydrate Compound

A mefenamic acid powder was milled with using a variety of the additive ratios of a carbohydrate compound relative to an organic compound.

Comparative Example 12

A mefenamic acid powder was milled without adding D-mannitol under following conditions.

100 mg of mefenamic acid powder used at Example 8 in EXPERIMENT 4, 0 mg of D-(−)-mannitol, 50 mg of sucrose fatty acid ester, 9 mg of sodium carboxymethyl cellulose and 110 mg of purified water were served on a glass disk of the foregoing Hoover muller and then kneaded by repeating five times to rotate the disk in 20 turns per time. Above-served contents formed a kind of dough during kneading and whereby the mefenamic acid powder was finely milled. 2 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of mefenamic acid powder obtained after above procedures was as follows: $D_{av}$=926 nm, the value of $D_{10}$=155 nm, the value of $D_{50}$=276 nm, and the value of $D_{90}$=3673 nm.

Comparative Example 13

A mefenamic acid powder was milled under the condition using D-mannitol of 0.1 times by mass relative to the mefenamic acid powder. Specifically, the mefenamic acid powder was milled and then subjected to a dispersion treatment under the same conditions as Comparative Example 12 except both milling with adding 10 mg of D-(−)-mannitol and weighing 4 mg of the dough obtained after milling into the foregoing glass vial. As a result, the particle diameter distribution of mefenamic acid powder obtained after above procedures was as follows: $D_{av}$=1013 nm, the value of $D_{10}$=212 nm, the value of $D_{50}$=467 nm, and the value of $D_{90}$=1722 nm.

Example 101

A mefenamic acid powder was milled under the condition using D-mannitol of 0.3 times by mass relative to the mefenamic acid powder. Specifically, the mefenamic acid powder was milled and then subjected to a dispersion treatment under the same conditions as Comparative Example 12 except both milling with adding 33 mg of D-(−)-mannitol and weighing 5 mg of the dough obtained after milling into the foregoing glass vial. As a result, the particle diameter distribution of mefenamic acid nano-powder obtained after above procedures was as follows: $D_{av}$=326 nm, the value of $D_{10}$=150 nm, the value of $D_{50}$=265 nm, and the value of $D_{90}$=495 nm.

Example 102

A mefenamic acid powder was milled under the condition using D-mannitol of 0.5 times by mass relative to the mefenamic acid powder. Specifically, the mefenamic acid powder was milled and then subjected to a dispersion treatment under the same conditions as Comparative Example 12 except both milling with adding 50 mg of D-(−)-mannitol and weighing 7 mg of the dough obtained after milling into the foregoing glass vial. As a result, the particle diameter distribution of mefenamic acid nano-powder obtained after above procedures was as follows: $D_{av}$=382 nm, the value of $D_{10}$=169 nm, the value of $D_{50}$=316 nm, and the value of $D_{90}$=573 nm.

Example 103

A mefenamic acid powder was milled under the condition using D-mannitol of 1.0 time by mass relative to the mefenamic acid powder. Specifically, the mefenamic acid powder was milled and then subjected to a dispersion treatment under the same conditions as Comparative Example 12 except both milling with adding 100 mg of D-(−)-mannitol and weighing 10 mg of the dough obtained after milling into the foregoing glass vial. As a result, the particle diameter distribution of mefenamic acid nano-powder obtained after above procedures was as follows: $D_{av}$=267 nm, the value of $D_{10}$=125 nm, the value of $D_{50}$=217 nm, and the value of $D_{90}$=404 nm.

Example 104

A mefenamic acid powder was milled under the condition using D-mannitol of about 3.3 times by mass relative to the mefenamic acid powder. Specifically, the mefenamic acid powder was milled and then subjected to a dispersion treatment under the same conditions as Comparative Example 12 except both milling with adding 325 mg of D-(−)-mannitol and weighing 10 mg of the dough obtained after milling into the foregoing glass vial. As a result, the particle diameter distribution of mefenamic acid nano-powder obtained after above procedures was as follows: $D_{av}$=247 nm, the value of $D_{10}$=99 nm, the value of $D_{50}$=198 nm, and the value of $D_{90}$=403 nm.

Example 105

A mefenamic acid powder was milled under the condition using D-mannitol of 30 times by mass relative to the mefenamic acid powder. Specifically, 10 mg of mefenamic acid powder, 300 mg of D-(−)-mannitol, 5 mg of sucrose fatty acid ester, 1 mg of sodium carboxymethyl cellulose and 200 mg of purified water were served on a glass disk of the foregoing Hoover muller and then kneaded by repeating five times to rotate the disk in 20 turns per time. Above-served contents formed a kind of dough during kneading and whereby the mefenamic acid powder was finely milled. 100 mg of the dough obtained after milling was weighed into a 50-mL glass vial and then added 5 mL of a mixed solution of 0.1% sodium dodecylsulfate and 0.01% hydrogenated soy bean lecithin. Then, the solution obtained above was subjected to a dispersion treatment by using the foregoing bath-type ultrasonic disperser for 1 to 2 minutes. As a result, the particle diameter distribution of mefenamic acid nano-powder obtained after above procedures was as follows: $D_{av}$=271 nm, the value of $D_{10}$=126 nm, the value of $D_{50}$=227 nm, and the value of $D_{90}$=403 nm.

Example 106

A mefenamic acid powder was milled under the condition using D-mannitol of 50 times by mass relative to the mefenamic acid powder. Specifically, the mefenamic acid powder was milled and then subjected to a dispersion treatment under the same conditions as Example 105 except both milling with adding 500 mg of D-(−)-mannitol and weighing 150 mg of the dough obtained after milling into the foregoing glass vial. As a result, the particle diameter distribution of mefenamic acid nano-powder obtained after above procedures was as follows: $D_{av}$=245 nm, the value of $D_{10}$=117 nm, the value of $D_{50}$=207 nm, and the value of $D_{90}$=358 nm.

Example 107

A mefenamic acid powder was milled under the condition using D-mannitol of 100 times by mass relative to the mefenamic acid powder. Specifically, the mefenamic acid powder was milled and then subjected to a dispersion treatment under the same conditions as Example 105 except both milling with adding 1000 mg of D-(−)-mannitol and 250 mg of purified water and weighing 300 mg of the dough obtained after milling into the foregoing glass vial. As a result, the particle diameter distribution of mefenamic acid nano-powder obtained after above procedures was as follows: $D_{av}$=264 nm, the value of $D_{10}$=132 nm, the value of $D_{50}$=217 nm, and the value of $D_{90}$=386 nm.

Table 15 shows the particle diameter distributions of mefenamic acid powders prepared in Comparative Examples 12, 13 and Examples 101 to 107.

TABLE 15

| | | Additive ratio of a carbohydrate compound | Particle diameter distibution (nm) | | | | | | | |
|---|---|---|---|---|---|---|---|---|---|---|
| | | | Before milling | | | | After milling | | | |
| Organic compound | Carbohydrate compound | (times) | Dav | D10 | D50 | D90 | Dav | D10 | D50 | D90 |
| Comparative Example 12 | Mef | Man | 0 | 16130 | 770 | 13290 | 35550 | 926 | 155 | 276 | 3673 |
| Comparative Example 13 | | | 0.1 | | | | | 1013 | 212 | 467 | 1722 |
| Example 101 | | | 0.3 | | | | | 326 | 150 | 265 | 495 |
| Example 102 | | | 0.5 | | | | | 382 | 169 | 316 | 573 |
| Example 103 | | | 1 | | | | | 267 | 125 | 217 | 404 |
| Example 104 | | | 3.3 | | | | | 247 | 99 | 198 | 403 |
| Example 105 | | | 30 | | | | | 271 | 126 | 227 | 403 |
| Example 106 | | | 50 | | | | | 245 | 117 | 207 | 358 |
| Example 107 | | | 100 | | | | | 264 | 132 | 217 | 386 |

As shown clearly from Table 15, the organic compound nano-powder with an average particle diameter of 500 nm or less and a 90%-diameter of less than 1500 nm was successfully produced when an organic compound powder was milled under the condition using the carbohydrate compound with the additive ratio of 0.3 times or more by mass relative to the organic compound powder.

INDUSTRIAL APPLICABILITY

The present invention can be used in such fields as a drug, a health food and a cosmetic.

The invention claimed is:

1. A method for producing an organic compound nano-powder comprising:
   mixing a granular organic compound, a granular sugar compound comprising at least any one of a granular sugar and a granular sugar alcohol and with amount of 0.3 times or more by mass relative to amount of the organic compound, and liquid in which the organic compound is insoluble or poorly soluble in a kneader;
   wet-milling the organic compound using the granular sugar compound as a grinding medium after the mixing so that an average particle diameter thereof becomes 500 nm or less and a 90%-diameter thereof becomes less than 1500 nm; and
   wherein the wet-milling of the organic compound is carried out while kneading the mixture obtained after the mixing in a kneader.

2. The method for producing an organic compound nano-powder according to claim 1, wherein the granular sugar compound is in an amount of 0.5 to 30 times by mass relative to amount of the organic compound.

3. The method for producing an organic compound nano-powder according to claim 1, wherein the mixing is carried out with adding a physiologically acceptable polyol as liquid in which the organic compound is insoluble or poorly soluble.

4. The method for producing an organic compound nano-powder according to claim 1, wherein a drying is carried out after the milling.

5. The method for producing an organic compound nano-powder according to claim 1, wherein the granular sugar compound is one or more kinds selected from the group consisting of mannitol, maltitol, xylitol, erythritol, glucose, fructose, inositol, lactose, trehalose, cellobiose and dextrin.

6. The method for producing an organic compound nano-powder according to claim 1, wherein a physiologically acceptable salt is further mixed in the process of the mixing.

7. The method for producing an organic compound nano-powder according to claim 6, wherein the physiologically acceptable salt is sodium chloride.

8. The method for producing an organic compound nano-powder according to claim 1, wherein the organic compound is one or more kinds selected from the group consisting of clarithromycin, fexofenadine hydrochloride, fluorometholone, curcuminoid, curcumin, rutin, mefenamic acid, acetaminophen, ibuprofen, amphotericin B, diclofenac sodium, indomethacin, felbinac, pranlukast hydrate, dexamethasone and fenofibrate.

9. The method for producing an organic compound nano-powder according to claim 1, wherein the mass ratio of the granular sugar compound to the liquid is 1.75-to-1 or more.

10. The method for producing an organic compound nanopowder according to claim 1, wherein the granular sugar compound comprises an average particle diameter of 10-631 microns.

* * * * *